United States Patent
Hilton et al.

(10) Patent No.: US 11,980,721 B2
(45) Date of Patent: *May 14, 2024

(54) CATHETER WETTING DEVICES

(71) Applicant: CONVATEC LIMITED, Flintshire (GB)

(72) Inventors: Gareth J. Hilton, Flintshire (GB); Colin V. Wood, Flintshire (GB); Manjunath L. Penagondla, Flintshire (GB); Stefan R. Taal, Flintshire (GB); James R. Hance, Flintshire (GB)

(73) Assignee: ConvaTec Limited, Flintshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/883,924

(22) Filed: Aug. 9, 2022

(65) Prior Publication Data
US 2022/0379075 A1 Dec. 1, 2022

Related U.S. Application Data

(63) Continuation of application No. 16/956,085, filed as application No. PCT/IB2018/001539 on Dec. 21, 2018, now Pat. No. 11,420,017.

(60) Provisional application No. 62/610,110, filed on Dec. 22, 2017.

(30) Foreign Application Priority Data

Dec. 27, 2017 (GB) ...................................... 1721955

(51) Int. Cl.
*A61M 25/00* (2006.01)
*A61M 39/10* (2006.01)

(52) U.S. Cl.
CPC ...... *A61M 25/002* (2013.01); *A61M 25/0017* (2013.01); *A61M 39/10* (2013.01); *A61M 2025/0062* (2013.01); *A61M 2210/1089* (2013.01)

(58) Field of Classification Search
CPC ............ A61M 25/002; A61M 25/0017; A61M 2025/0062
See application file for complete search history.

(56) References Cited

U.S. PATENT DOCUMENTS

| | | | |
|---|---|---|---|
| 5,743,359 A * | 4/1998 | Parnell ...................... | F16N 7/12 184/88.1 |
| 6,554,808 B1 * | 4/2003 | Cook .............. | A61M 25/09041 604/265 |
| 8,181,778 B1 * | 5/2012 | van Groningen .. | A61M 25/0111 206/364 |
| 11,400,257 B2 | 8/2022 | Tierney et al. | |

(Continued)

OTHER PUBLICATIONS

US 11,433,217 B2, 09/2022, Erbey, II (withdrawn)
US 11,433,219 B2, 09/2022, Erbey, II (withdrawn)

*Primary Examiner* — Catharine L Anderson
*Assistant Examiner* — Arjuna P Chatrathi
(74) *Attorney, Agent, or Firm* — Taft Stettinius & Hollister LLP; Ryan O. White; Derek B. Lavender

(57) ABSTRACT

A wetting device for wetting a catheter. The wetting device has an enclosure bounding the wetting device and enclosing a chamber, the enclosure having at least two wetting device apertures in a surface of the enclosure though which a catheter tube passes. The wetting device also has a port disposed through the enclosure thereof for loading wetting agent into the chamber.

18 Claims, 22 Drawing Sheets

(56) References Cited

U.S. PATENT DOCUMENTS

| | | |
|---|---|---|
| 11,420,017 B2 | 8/2022 | Hilton et al. |
| 11,458,283 B2 | 10/2022 | Fletter et al. |
| 2016/0038717 A1* | 2/2016 | Murray .............. A61M 25/0111 604/544 |
| 2016/0339205 A1* | 11/2016 | Foley .................... A61M 27/00 |
| 2022/0211973 A1 | 7/2022 | Palmer |
| 2022/0241557 A1 | 8/2022 | Erbey, II et al. |
| 2022/0362515 A1 | 11/2022 | Erbey, II et al. |
| 2022/0379075 A1 | 12/2022 | Hilton et al. |

* cited by examiner

SECTION B-B

SECTION C-C

CATHETER WETTING DEVICES

CROSS-REFERENCE TO RELATED APPLICATIONS

This application is a continuation of U.S. application Ser. No. 16/956,085 filed on Jun. 19, 2020 and which is a national phase entry of International Application No. PCT/IB2018/001539 filed Dec. 21, 2018, which claims the benefit of U.S. Provisional Application No. 62/610,110 filed Dec. 22, 2017, and GB 1721955.1, filed Dec. 27, 2017, each of which is incorporated by reference herein in its entirety.

This application incorporates in its entirety International Application No. PCT/IB2018/001543 titled "Intermittent Urinary Catheter Device and Case Therefor", filed on Dec. 21, 2018. This application also incorporates in its entirety International Application No. PCT/IB2018/001540 titled "Female Catheter Locator Tip", filed on Dec. 21, 2018.

BACKGROUND OF THE DISCLOSURE

Field of the Disclosure

The present disclosure relates to devices for applying a fluid to an outer surface of a medical tube, including a medical tube having a hollow lumen. In certain embodiments, the present disclosure relates to such wetting devices for medical tubes in urinary catheters, and packages therefore.

Description of Related Art

A catheter is a tubular medical device designed for insertion into canals, vessels, passageways or body cavities to permit injection, drainage or withdrawal of fluids or substances or to maintain the openness of a passageway. Catheters can be used to transfer fluids and fluidized substances. For example, a catheter can be used as a drainage tube for insertion into the bladder via the urethra to drain the bladder.

An indwelling urinary catheter is left in place for a specified period of time. An intermittent urinary catheter is generally removed after a single use, e.g., when a bladder is emptied.

In a female, a urinary catheter tube is typically inserted into the urinary tract through the urethral meatus. In a male, a urinary catheter tube is typically inserted into the urinary tract through the penis.

When inserting a urinary catheter, lubrication may minimize friction, infection risk, and trauma to the urethra. Some urinary catheters are pre-lubricated and self-contained. A disadvantage of such a pre-lubricated, self-contained catheter is that the lubricant can become dispersed throughout the catheter package so that components other than the catheter tube, such as the handling sleeve and funnel, can become lubricated. This unwanted lubrication can make it difficult to manipulate the catheter, advance the catheter and wastes lubricant. Additionally, it can be difficult to hold the catheter, handling sleeve or other components and guide the catheter at the same time, particularly if a patient is attempting self-catheterization. Further, an excess quantity of lubricant can result in a significant mess and inconvenience to the user, because it is easy to spill such quantities from either rigid or flexible packaging. Still further, a lubricant may not be retained in one area of a package but may migrate into the urine-collection chamber or pouch, causing the walls of the chamber or pouch to collapse and/or stick together, thus making voiding more difficult.

SUMMARY OF THE DISCLOSURE

Provided herein, in some aspects, are wetting devices for a tube, comprising: an enclosure enclosing a chamber having at least two apertures through which the tube can traverse; a wetting applicator located in the chamber having an opening through which the tube can traverse; wherein the wetting applicator is configured to release a wetting agent upon pressure applied within the chamber to the wetting applicator. In some instances, the tube is a medical tube. In some instances, the medical tube is a catheter. In some instances, the catheter is a urinary catheter. In some instances, the urinary catheter is suitable for insertion in a male urethra. In some instances, the urinary catheter is suitable for insertion in a female urethra. In some instances, the wetting applicator is compressible. In some instances, the wetting applicator is infused with the wetting agent. In some instances, the wetting applicator comprises the wetting agent. In some instances, the enclosure comprises a port for adding the wetting agent to the wetting applicator. In some instances, the medical tube comprises or is integrated with a polymer, such as a hydrophilic polymer. In some instances, the medical tube is coated with a polymer, such as a hydrophilic polymer. In some embodiments, the medical tube comprises or is integrated with a polymer mixture of a thermoplastic or thermo-curing polymer base material and an amphiphilic block copolymer, e.g., as disclosed in WO 2011/051439 filed Oct. 29, 2010, the entirety of which is incorporated by reference herein. In some embodiments, the medical tube is coated with the polymer mixture of a thermoplastic or thermos-curing polymer base material and amphiphilic block copolymer, e.g., as disclosed in WO 2011/051439.

Provided herein, in some aspects, are systems that comprise a wetting device of any one of the preceding claims and a catheter tube. In some instances, systems comprise a connector connecting the catheter tube to a funnel. In some instances, the connector is positioned within the wetting device. In some instances, the connector has a first plug at a first end and a second plug at a second end, wherein the first plug and the second plug seal the wetting device until the connector is pulled through the wetting device. In some instances, at least a region of the connector comprises a diameter that is larger than the diameter of the opening of the wetting applicator. In some instances, the connector applies pressure to the wetting applicator to release the wetting agent as the catheter tube is moved through the wetting device. In some instances, the catheter tube has a non-hydrophilic surface. In some instances, systems comprise a handling sleeve, wherein the handling sleeve extends over the catheter tube as the catheter tube is removed from the enclosure. In some instances, systems comprise a wetting agent. In some instances, the wetting agent lubricates the catheter tube.

Provided herein, in some aspects, are methods of using a system disclosed herein, comprising removing a catheter tube from a package and wetting the catheter tube, wherein the removing and wetting occurs substantially simultaneously. In some instances, removing the catheter tube from a package results in wetting the catheter tube. In some instances, systems comprise a handling sleeve, wherein the handling sleeve is substantially simultaneously extended over the catheter tube as the wetting agent is distributed to the catheter tube. In some instances, methods comprise adding a wetting agent to the wetting device through a port in the enclosure of the wetting device. In some instances, methods do not require adding a wetting agent to the wetting device. In some instances, methods comprise opening a package and pulling a catheter tube out of the package by its funnel, thereby wetting the catheter tube. In some instances, methods comprise inserting the catheter tube into a urethra immediately after removing the catheter tube from the package.

The above and other objects, features, and advantages of the present disclosure will be apparent and understood by those skilled in the art from the following detailed description, drawings, and accompanying claims.

Figure 1:
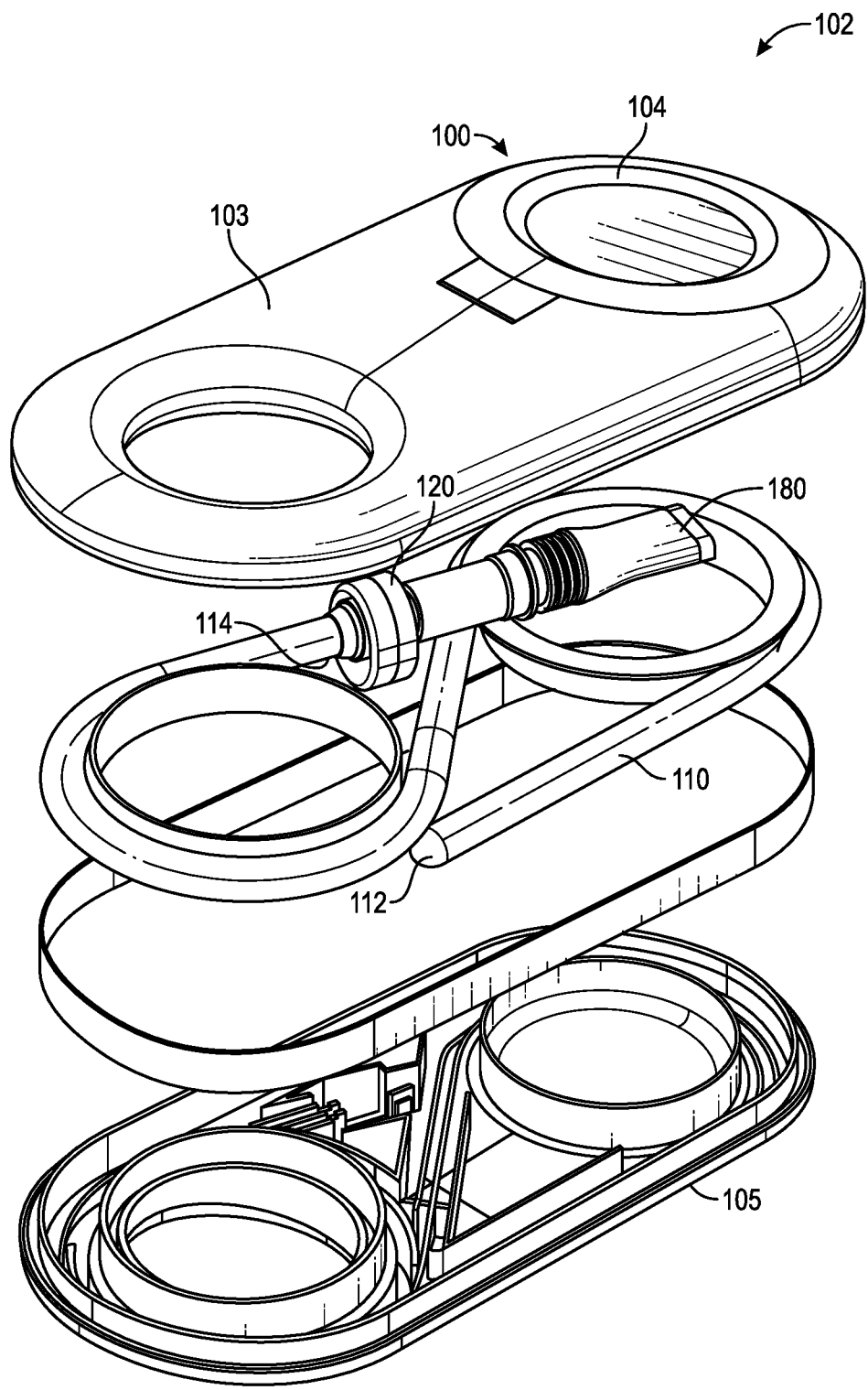
FIG. 1 shows an exemplary exploded perspective view of a catheter package showing a wetting device.

The accompanying drawings illustrate presently preferred embodiments of the present disclosure directed to urinary catheters, and together with the general description given above and the detailed description given below, explain the principles of the present disclosure. Reference to these disclosed and specifically described exemplary wetting devices with a urinary catheter are not meant to limit the principles and application of the disclosed wetting device that are equally applicable to other suitable medical articles such as but not limited to a feeding tube, trachea tube, insemination device, balloon catheter, guidewire, and an endovascular probe. Reference to fluid, liquid, lubricant or other material disposed in the wetting device is not meant to limit the principles and application of the disclosed wetting devices and such material may be equally applicable to specific embodiments, other suitable medical articles and modifications thereof.

As shown throughout the drawings, like reference numerals designate like or corresponding parts.

DETAILED DESCRIPTION OF THE DISCLOSURE

The present disclosure provides wetting devices for wetting medical tubing. In some instances, wetting comprises lubricating. In some instances, wetting occurs at a time of use or shortly therebefore.

The present disclosure provides wetting devices that can be used for wetting catheters. In some instances, wetting devices disclosed herein are used for indwelling catheters. In some instances, wetting devices disclosed herein are used for intermittent catheters. By way of non-limiting example, wetting devices disclosed herein may be used with urinary catheters. In some instances, the urinary catheter is a male urinary catheter (e.g., suitable for use with a male urethra). In some instances, the urinary catheter is a female urinary catheter (e.g., suitable for use with a female urethra). Also, by way of non-limiting example, wetting devices disclosed herein can be used for wetting feeding tubes before its insertion into the esophagus. Wetting devices disclosed herein can also be used for wetting a tracheal tube before its insertion into the trachea. Wetting devices disclosed herein are not limited in use, and are intended to be used for inserting devices, such as catheters, into various body passageways and cavities. Body passageways and cavities include, but are not limited to, a urethra, trachea, esophagus, ear canal, sinus cavity, blood vessel, vagina, and rectum.

As discussed in greater detail herein, the present disclosure provides for a wetting device that comprises a chamber defined by an enclosure having at least two apertures; and a wetting applicator having an opening, the wetting applicator disposed in the chamber with the opening between the two apertures so that as a catheter tube traverses the chamber from one body surface to the other body surface, an outer surface of the catheter tube is properly wetted by the wetting applicator. The wetting device may have a body that has a plurality of walls including a first end wall opposite a second end wall. In some instances, the at least two apertures are in axial alignment. In some instances, the wetting applicator is compressible and impregnable with the wetting agent. In some instances, the wetting applicator is loadable with a wetting agent. In some instances, the wetting device comprises a port disposed through the enclosure thereof for loading a wetting agent into the chamber.

The volumes and dimensions of chambers disclosed herein are dependent upon a number of factors, including, but not limited to, type of coating on the tubing, the amount of fluid required to hydrate the coating, the diameter of the tube, the density of the foam, the absorbency of the foam and the length of tubing that requires hydrating. However, the volumes and dimensions should be appropriately sized for a convenient and discreet catheter device. In some instances, the volume of the chamber is between about 1 $cc^3$ and 15 $cc^3$. In some instances, the volume of the chamber is between about 1 $cc^3$ and 10 $cc^3$. In some instances, the volume of the chamber is between about 1 $cc^3$ and 5 $cc^3$. In some instances, the volume of the chamber is between about 3 $cc^3$ and 10 $cc^3$. In some instances, the volume of the chamber is between about 4 $cc^3$ and 10 $cc^3$. In some instances, the volume of the chamber is between about 5 $cc^3$ and 10 $cc^3$. In some instances, the volume of the chamber is between about 1 $cc^3$ and 15 $cc^3$.

Further provided herein are systems that comprise wetting devices and catheter tubes. Catheter tubes generally have an insertion end and a drainage end. The catheter tube can be initially positioned outside the chamber of the wetting device. Systems disclosed herein may comprise a connector having an axial through bore in communication with the catheter tube drainage end. The connector may span the chamber from the first end wall to the second end wall to seal the two apertures so the chamber is sealed in its pre-use state. The connector may be slideable with respect to the chamber when the catheter is in use so the insertion end of the catheter tube traverses the apertures of the first end wall and the second end wall of the chamber. In some instances, the connector is a cylindrical member having, in order, a first section, a second section and a third section. The first section and the third section may have an inner diameter greater than an inner diameter of the second section. In some instances, the first section seals one of the two apertures and the third section seals the second of the two apertures. In some instances the catheter tube is connected to a funnel. In some instances, the funnel is disposed on a side of the chamber that is opposite to the catheter tube and in communication with the connector. In some instances, the two apertures are unsealed when the funnel is pulled through the chamber. In some instances, the system comprises a package. In some instances, the wetting device is integrated in the package. In some instances, the catheter tube is in the package in a configuration in the package selected from the group consisting of straight, coiled, and curved, and a combination thereof.

Further provided herein are methods of using wetting devices disclosed herein. The method may comprise pulling or pushing a catheter tube through a wetting device disclosed herein such that an outer surface of the catheter tube is lubricated by the wetting applicator as the catheter traverses the chamber from the first end wall to the second end wall. In some instances, the wetting applicator is disposed in the chamber with the opening in alignment with the two apertures, before use. Methods disclosed herein may comprise providing a sealed chamber having two aligned apertures disposed at opposing ends of the chamber with a connector that spans the chamber with the connector fluidly connecting a catheter to a funnel, the catheter and funnel disposed outside the chamber; drawing the catheter through the chamber; thereby applying a wetting agent to a surface of the catheter when in the chamber. In some instances, the method comprises removing excess lubricant from the surface of the catheter before exiting the chamber. In some instances, methods disclosed herein comprise applying a wetting agent to the wetting device. In some instances, methods disclosed herein comprise applying a wetting agent to a wetting applicator of the wetting device. In some instances, methods disclosed herein comprise loading a chamber of the wetting device with a wetting agent through a port of the enclosure of the wetting device.

In some instances, wetting devices disclosed herein wet a catheter tube during removal of the catheter from a package. In some instances, the package is a case. In some instances, the wetting device remains in the package after the catheter tube is removed from the package. In some instances, the wetting device is attached to the package. In some instances, wetting devices disclosed herein are configured to be activated to wet a catheter tube when the catheter tube is removed from a package, resulting in wetting the catheter tube during removal of the catheter from the package. In some instances, the wetting device configured to be activated comprises a material that releases a wetting agent when the wetting device is squeezed or compressed. In some instances, the wetting device configured to be activated comprises a wetting agent that is retained by a seal, wherein the seal is broken upon pressure applied to the wetting device, thereby releasing the wetting agent to make contact with the catheter tube. Wetting the catheter during removal from the package may allow for the catheter tube to be inserted into a urethra by smooth movement with minimal friction.

In some instances, wetting devices disclosed herein are bounded by an enclosure (e.g., case, shell or container), wherein the enclosure encloses a chamber. In some instances, the chamber contains other components of the wetting device, such as the wetting agent. The enclosure may be rigid. The enclosure may be made of a hard plastic. The enclosure may be sufficiently rigid to prevent external pressure on the contents of the enclosure. The enclosure may be made of a semi-rigid, flexible material (e.g., polymer, rubber, plastic), but sufficiently rigid to prevent external pressure on the contents of the enclosure. The enclosure may be leak-resistant. The enclosure may be leak-proof. The enclosure may be leak-resistant when in use. The enclosure may be leak-proof when in use. The enclosure may be leak-resistant before use. The enclosure may be leak-proof before use. The enclosure may be leak-resistant after use. The enclosure may be leak-proof after use. In some instances, the enclosure has a rectangular shape, see, e.g., FIGS. 5 and 6. In some instances, the enclosure has a cylindrical shape, see, e.g., FIG. 13. It should be appreciated that any shape or combination of shapes can be suitable for use with the present wetting device provided the same principles and effects as those described more particularly throughout are maintained.

Forward sections and rearward sections, as disclosed herein may be made of a material that has a low moisture vapor transmission rate (MVTR) (also referred to as water vapor transmission rate (WVTR)) that is a measure of the passage of water vapor through a substance. A low MVTR is desired so that moisture/lubricant on/in wetting applicator is retained. Having a low and controlled MVTR is helpful in achieving the required quality, safety, and shelf life. In some instances, forward sections and rearward sections are made of polypropylene (PP) or polyethylene terethalate (PET), or another suitable material with similar low MVTR. Plastics with a moisture barrier coating, such as a SiOx layer, would also be effective at reducing the MVTR to desired levels. In some instances, the material has an MVTR below 1.5 $(g*mm)/(m^2*24\ h)$. In some instances, the material has an MVTR below 1.0 $(g*mm)/(m^2*24\ h)$.

In some instances, the wetting device has at least two wetting device apertures through which the catheter tube passes. In some instances, the wetting device is bounded by an enclosure, wherein there is at least two wetting device apertures in a surface of the enclosure. In some instances, the wetting device comprises two wetting device apertures. In some instances, the wetting device comprises at least two wetting device apertures. In some instances, the diameter of the catheter tube is the same as at least one wetting device aperture. In some instances, at least one wetting device aperture is circular. In some instances, at least one wetting device aperture is oval. In some instances, at least one wetting device aperture is polygonal. In some instances, at least one wetting device aperture comprises a slit in the enclosure. In some instances, at least one wetting device aperture comprises a plurality of slits in the enclosure, forming a cross, asterisk, or star-like opening. Regardless of the aperture shape, wetting device apertures disclosed herein are generally configured to be sufficiently snug around a catheter tube, such that any wetting agent within the enclosure (e.g., in the chamber) of the wetting device cannot pass through the wetting device aperture unless it is on the catheter tube. Moreover, wetting device apertures disclosed herein may be sufficiently snug around the catheter tube to remove excess wetting agent from the surface of the catheter tube as the catheter tube is exiting the chamber.

In some instances, the two apertures have unequal diameters. In some instances, the two apertures are each sprung against the connector to create seals. In some instances, at least one of the two apertures is conical so that the inner diameter of the one aperture decreases in a direction away from the chamber.

In some instances, a portion of a wetting device enclosure disclosed herein defines the perimeter of the wetting device aperture. The portion of the enclosure may consist of the same material as the remaining enclosure. The portion of the enclosure may comprise a different material from that of the remaining enclosure. In some instances, the perimeter of the wetting device aperture comprises a material that is more rigid than that of the remaining enclosure. In some instances, the perimeter of the wetting device aperture comprises a material that is more soft and flexible than that of the remaining enclosure. In some instances the material comprises a foam. In some instances, the material comprises a rubber. In some instances the material comprises a polymer. In some instances the material comprises a plastic.

In some instances, the at least one wetting device aperture is circular and the catheter tube is cylindrical. In some instances, the diameter of the catheter tube is smaller than the diameter of the at least one wetting device aperture. In some instances, the diameter of the catheter tube is only sufficiently smaller than the diameter of the at least two wetting device apertures to allow the catheter tube to pass through the at least one wetting device aperture. In some instances, the diameter of the catheter tube is about 0.001% to about 1% smaller than the diameter of the at least one aperture. In some instances, the diameter of the catheter tube is about 0.01% to about 1% smaller than the diameter of the at least one aperture. In some instances, the diameter of the catheter tube is about 0.1% to about 1% smaller than the diameter of the at least one aperture. In some instances, the diameter of the catheter tube is about 0.001% to about 0.01% smaller than the diameter of the at least one aperture. In some instances, the diameter of the catheter tube is about 0.01% to about 0.1% smaller than the diameter of the at least one aperture.

In some instances, wetting devices disclosed herein comprise a wetting applicator. In some instances, wetting devices disclosed herein comprise a wetting applicator within a chamber of the wetting device. In some instances, wetting applicators disclosed herein apply a wetting agent to the catheter tube. In some instances, wetting applicators disclosed herein are capable of distributing a wetting agent on to a catheter tube. In some instances, wetting applicators disclosed herein are capable of releasing a wetting agent on to a catheter tube. In some instances the chamber is configured to allow a catheter tube to pass through it, transferring the wetting agent or another suitable material from the wetting applicator onto the catheter tube. In some instances, the catheter tube contacts the wetting applicator as it passes through the chamber. In some instances, the catheter tube passes through the wetting applicator as it passes through the chamber. In some instances, the catheter tube applies pressure to the wetting applicator as it passes through the chamber, thereby releasing a wetting agent from the wetting applicator on to the catheter tube. Because the pressure on the wetting applicator is generated by the movement of the catheter tube through the wetting device, only removal of the catheter tube from the package is necessary to obtain the wetted catheter tube. This is advantageous over devices where wetting requires a separate movement or action, such as squeezing a chamber or tube with wetting agent to distribute wetting agent over the catheter tube. A requirement for two separate actions may require coordination that some users have difficulty obtaining. The requirement for this coordination may also risk dropping or damaging the device, resulting in a contaminated or unusable device. The requirement for this coordination may also result an embarrassing or inconvenient mess caused by spilt wetting agent.

In some instances, wetting applicators disclosed herein are present within the enclosure of the wetting device. In some instances, wetting applicators disclosed herein are present within the enclosure of the wetting device before use. In some instances, wetting applicators disclosed herein are present with the wetting agent within the enclosure of the wetting device before use. In some instances, wetting applicators disclosed herein hold the wetting agent within the enclosure of the wetting device before use. In some instances, the wetting applicators disclosed herein are present within the enclosure of the wetting device after use. In some instances, wetting devices disclosed herein comprise a wetting applicator that holds a wetting agent until a catheter tube is removed from its package or put into use. In some instances, the wetting applicator that holds a wetting agent until use is in an enclosure that is sealed by a connector until use. This combination of a wetting applicator that holds a wetting agent until use and an enclosure that is sealed by a connector until use provides added assurance that the wetting agent will remain contained in the wetting device until use. A wetting agent that remains contained and sealed in a wetting device until use is more desirable relative to a wetting agent that is only held by a wetting applicator or only sealed until use, because there is less chance of wetting agent leaking onto parts of the catheter system that should not be exposed to wetting agent, (e.g., a handle, case, funnel).

In some instances, wetting devices disclosed herein comprise a wetting applicator, wherein the wetting applicator is capable of applying a wetting agent. In some instances, wetting applicators disclosed herein comprise a wetting agent. In some instances, wetting applicators disclosed herein contain a wetting agent. In some instances, wetting applicators disclosed herein hold a wetting agent.

Wetting applicators disclosed herein may be flexible. The wetting applicator may be compressible. The wetting applicator may be soft. The wetting applicator may be spongy or squishy. The wetting applicator may be absorbent. The wetting applicator may be porous. The wetting applicator may be fibrous. The wetting applicator may release a wetting agent when pressure is applied to the wetting applicator. The wetting applicator may deform under pressure. In some instances, a wetting applicator may obtain a previous form after pressure is applied to the wetting applicator and subsequently removed. In some instances, a wetting applicator may remain deformed after pressure is applied to the wetting applicator. In some instances, a wetting applicator may remain compressed after pressure is applied to the wetting applicator.

In some instances, wetting devices disclosed herein comprise a wetting applicator that is compressible and impregnable with a wetting agent. In some instances, wetting applicators disclosed herein comprise a material that facilitates expansion of an opening therein over the widest diameters of a catheter tube, connector, or plug member. In some instances, the material facilitates expansion of the opening when the catheter tube is removal from a package or case. In some instances, the wetting applicator, or opening thereof, collapses or returns toward its original shape, making contact with the exterior surface of catheter tube as the catheter is withdrawn. In some instances, the wetting applicator, or opening thereof, retains its expanded form, maintaining contact with the exterior surface of catheter tube as the catheter is withdrawn.

Wetting applicators disclosed herein may comprise a flexible material such as a suitable foam. The foam may comprise a substance formed of varying compressible cell structures and pockets of air that can absorb liquid. In some instances, foam comprises polyethylene. In some instances, foam comprises polyurethane. In some instances, the foam is a polyurethane foam. In some instances, the foam is a polyethylene foam. In some instances, the foams is an open cell hydrophilic polyurethane foam, The foam may have a density of about 1 pcf to about 10 pcf. The foam may have a density of about 5 pcf. The foam may be non-swelling when exposed to water. The foam may swell by less than 1% to less than 10% when exposed to water. The foam may swell by less than 2% when exposed to water. A non-swelling foam may be particularly useful because the dimensions of the foam remain consistent regardless of level of saturation of the foam. The foam may have an absorbency greater than 2 g water/g foam. The foam may have an absorbency greater than 8 g water/g foam. The foam may have an absorbency greater than 2 g water/g foam, but less than 20 g water/g foam. Such an absorbency may ensure that the foam holds sufficient wetting agent. In some instances, the foam is a hydrophilic foam. A hydrophilic foam may allow the wetting agent to be readily absorbed into the foam during a filling process. Additional examples of wetting applicators are further described throughout the instant disclosure.

In some instances, wetting devices disclosed herein contain a wetting applicator, wherein the wetting applicator is dry. In some instances, wetting devices disclosed herein contain a wetting applicator, wherein the wetting applicator does not hold a wetting agent, but is capable of holding a wetting agent. In some instances, the wetting device is configured to receive a wetting agent after the wetting applicator is contained within the enclosure/chamber of the wetting device. In some instances, the wetting device comprises a port in the enclosure, through which a wetting agent can be added to a wetting applicator present in a chamber of the wetting device. The port may be located on a surface of the enclosure. See, e.g., FIGS. 6, 7, 13 and 14. Placement of the port is dependent upon the orientation of the assembly during the filling process. In some instances, it may be advantageous to fill the wetting device when the assembly is in the vertical orientation, in which case a filling hole shown in FIGS. 6 and 7 would be preferred. Otherwise the assembly may be in a horizontal orientation during filling, making the position of the filling hole shown in FIGS. 13 and 14 more preferred.

Wetting applicators may be sized to provide space between the wetting applicator and an inner surface of an enclosure of the wetting device. Wetting applicators may be sized to provide space between the wetting applicator and an inner surface of a chamber of the wetting device. For example, total volume of the wetting applicator may be smaller than the total volume of the chamber. In these instances, the wetting applicator may be referred to as a "floating applicator." A dry floating applicator may allow expansion of the wetting agent when a wetting agent is added during assembly. A wet floating applicator may allow for unintentional movement of the wetting applicator within the chamber without a squeezing force or pressure acting on the wetting applicator, which would otherwise unintentionally release the wetting agent result in uneven coating of the catheter tube. This may occur if the catheter tube where to be withdrawn at a slight angle (e.g., before catheter use).

In some instances, the wetting device comprises a wetting applicator, wherein the wetting applicator comprises at least one opening through which a catheter tube passes. In some instances, the opening has a diameter that is smaller than the diameter of the catheter tube. In some instances, the opening has a diameter that is the same diameter as that of the catheter tube. In some instances, the opening has a diameter that is larger than the diameter of the catheter tube. In some instances, an end of the catheter tube is attached to a connector described herein, and the opening has a diameter that is smaller than the diameter of the connector. In some instances, the opening has a diameter that is the same as the diameter of a connector. In some instances, the opening has a diameter that is smaller than the diameter of a connector so that the connector applies pressure on the wetting applicator as the connector passes through the wetting applicator. In some instances, the opening has a diameter that is smaller than the diameter of a catheter tube so that the catheter tube applies pressure on the wetting applicator as the catheter tube passes through the wetting applicator.

Generally, wetting devices disclosed herein comprise a wetting agent or are configured to be used with a wetting agent. Wetting agents, as used herein, include liquids and gels. In some instances, the wetting agent is a liquid. In some instances, the liquid comprises water. In some instances, the liquid is water. Suitable wetting agents for use with wetting devices disclosed herein include, but are not limited to, deionized water, purified water, a light viscosity silicone fluid, and a mild saline solution. Wetting agents can also contain anti-microbials. Non-limiting examples of anti-microbials include chlorhexidine gluconate. Wetting agents can also contain an analgesic. A non-limiting example of an analgesic is lidocaine. In some instances, the liquid is a solution. In some instances, the solution comprises a salt (e.g., a saline solution). In some instances, the solution comprises a lubricant. Non-limiting examples of lubricants include light viscosity silicone fluid or a lubricant gel. In some instances, the wetting agent is a gel. In some instances, the gel comprises carbomer. Non-limiting examples of gels include KY gel and other similar non-toxic lubricants. In some instances, In a male intermittent catheter embodiment, a minimum volume of 300 microlitres of wetting agent is required with the preferred volume being 400 microlitres of wetting agent when applying water to an approx. 30 cm long, CH14 (4.33 mm diameter) catheter with feel clean technology lubrication.

In some instances, wetting devices disclosed herein contain, or are capable of containing, a volume of wetting agent. The volume may be about 100 microliters to about 1 milliliter. The volume may be about 100 microliters to about 800 microliters. The volume may be about 100 microliters to about 600 microliters. The volume may be about 100 microliters to about 400 microliters. The volume may be about 200 microliters to about 1 milliliter. The volume may be about 200 microliters to about 800 microliters. The volume may be about 200 microliters to about 600 microliters. The volume may be about 200 microliters to about 400 microliters.

In some instances, wetting devices disclosed herein are configured to be used with a catheter tube, wherein the catheter tube is connected to a connector. By way of non-limiting example, the connector may be hollow and connect the catheter tube to a funnel for voiding fluids from the catheter tube. In some instances the chamber of the wetting device is configured to allow a connector to pass through it, followed by the catheter tube. In some instances, the connector passes through the wetting applicator as it passes through the chamber. In some instances, the connector applies pressure to the wetting applicator, thereby releasing the wetting agent from the wetting applicator on to the catheter tube. In some instances, the connector applies pressure to the wetting applicator as it passes through the chamber, thereby releasing a wetting agent from the wetting applicator on to the catheter tube as the catheter tube follows the connector through the chamber.

In some instances, wetting devices disclosed herein are configured to be used with a catheter tube, wherein the catheter tube is not connected to a connector. By way of non-limiting example, the catheter tube may connect directly to a funnel, handle, additional tube, bag, etc. In some instances, the catheter tube passes through the wetting applicator as it passes through the chamber. In some instances, a wetting agent is applied to catheter tube as it passes through the wetting applicator. In some instances, the catheter tube comprises a region with a larger diameter than that of the remaining catheter tube, (e.g., a bulge in the catheter tube). Due to its larger diameter, the region of the catheter tube may apply pressure to the wetting applicator, thereby releasing the wetting agent from the wetting applicator on to the catheter tube. In some instances, movement of the catheter tube through the wetting applicator initiates the release of a wetting agent from a wetting applicator on to the catheter tube.

In some instances, wetting devices disclosed herein are configured to be used with a catheter tube, wherein the catheter tube is not connected to a funnel. By way of non-limiting example, funnels disclosed herein may comprise at least one material selected from thermoplastic polyurethane (TPU), thermoplastic elastomers (TPE), and polyvinyl chlorides (PVC).

Wetting devices disclosed herein may comprise a plug, also referred to as a plug member herein. Plugs may create an interference fit with a seal of the chamber in order to achieve a desired seal. Sealing is required during storage and transportation of the chamber to prevent leakage or evaporation of the wetting agent should the chamber be provided pre-filled. Plug members can be integral to or disposed about connector. In some embodiments, plug members are formed from a different material than the connector. Other known methods for establishing the seal between plug members and apertures may also be suitable for use in accordance with the present disclosure.

In some embodiments, wetting devices disclosed herein comprise a chamber that is an enclosed space with at least two apertures positioned geometrically apart in the chamber. In some instances, a catheter tube is directly or indirectly connected to a connector, and the connector spans the chamber in a pre-use packaged state to seal the two apertures. The connector may be slideable in the chamber so that in an operative state for use, the catheter tube can be drawn through the chamber. A wetting agent may be disposed in the chamber to lubricate the catheter tube as it traverses the chamber.

In some embodiments, the chamber is defined by a plurality of walls with a first end wall and a second end wall separated by a space in the chamber. In some embodiments, the first end wall and the second end wall each have a pre-formed aperture disposed therethrough. The connector may span the chamber in a pre-use packaged state to seal the two apertures. The connector may be slideable in the chamber. The connector may be slideable in the chamber so that in an operative state for use, the catheter tube can be drawn through the chamber.

In another embodiment, the chamber is defined by a plurality of walls with a first end wall opposite to a second end wall along the axis of the catheter. At least one of the first and the second end walls may each have an aperture disposed therethrough. The connector may span the chamber in a pre-use packaged state to seal the two apertures. The connector may be slideable in the chamber. The connector may be slideable in the chamber so that in an operative state for use, the catheter tube can be drawn through the chamber.

The present disclosure also provides a wetting device that comprises: a chamber defined by a body having a hollow interior and two body surfaces separated in part by the hollow interior, each of the two body surfaces having an aperture; and a wetting applicator loadable with a wetting agent and having an opening, the wetting applicator disposed in the chamber with the opening between the two apertures so that as a catheter tube traverses the chamber from one body surface to the other body surface, an outer surface of the catheter tube is properly wetted by the wetting device.

In yet another embodiment, the chamber is enclosed by a plurality of walls with a first end wall opposite to a second end wall along the axis of the catheter. The first and the second end walls may each have an aperture disposed therethrough that are axially aligned. The present disclosure yet further provides such a wetting device that may apply or activate a wetting agent at the time and point of insertion to minimize the amount of liquid required and avoid excess unwanted quantities thereof.

The present disclosure further provides a system comprising a wetting device herein and a catheter tube. See, e.g., FIGS. 1 and 2. In some instances, the catheter tube is connected to a funnel. In some instances, the catheter tube comprises a connector that connects the catheter tube to the funnel. In some instances, the connector is located within a chamber of the wetting device. In some instances, the system comprises a case or packaging that holds the wetting device and catheter tube before use. See, e.g., FIGS. 1 and 2. In some instances, the case or packaging holds the wetting device and catheter tube after use.

In some aspects, the instant disclosure provides for systems that comprise wetting devices and catheter tubes disclosed herein. In some instances, wetting devices are configured to be used with a catheter tube disclosed herein. Catheters tubes can be straight, curved, or coiled in packages. Catheters tubes may be flexible to allow bending without kinking. Catheter tubes disclosed herein are made of a flexible material such as a thermoplastic elastomer. Thermoplastic elastomers are sometimes also referred to as thermoplastic rubbers. Thermoplastic elastomers include, but are not limited to, a class of copolymers or a physical mix of polymers (usually a plastic and a rubber) that consist of materials with both thermoplastic and elastomeric properties.

Thermoplastic elastomers may provide advantages typical of both rubbery materials and plastic materials. The benefit of using thermoplastic elastomers is the ability to stretch to moderate elongations and return to its near original shape creating a longer life and better physical range than other materials. Alternative and additional materials for catheters tubes include polyvinyl chlorides and rubber. Other materials include those described in U.S. Pat. No. 9,186,438, which is incorporated by reference in its entirety herein. U.S. Pat. No. 9,186,438 generally describes polymer mixtures comprising a first and a second polymer, with the first polymer being a thermoplastic or thermo-curing polymer and the second polymer being an amphiphilic block copolymer possessing both hydrophilic and lipophilic properties. The polymer mixtures maintain a low kinetic coefficient of friction even when the surface is scraped so that the lubricious properties are maintained throughout the entire surface of the article.

In certain embodiments, catheter tubes disclosed herein maintain a low friction property even when a surface thereof is scraped to maintain lubricous properties throughout the entire surface. For example, U.S. Pat. No. 9,186,438 to Gravesen et al. for "Medical Tube Article" discloses a medical tube article comprising a polymer mixture of a thermoplastic or thermocuring polymer base material and an amphiphilic block copolymer. Advantageously, in some embodiments, catheter tubes disclosed herein can be sufficiently wetted by simply wiping an outer surface of the catheter tube with water or aqueous solution. The hydrophilic part of the amphiphilic block copolymer may diffuse to the surface allowing for a thinner coating layer of lubricant to be effectively used.

In some embodiments, the catheter tube comprises or is integrated with a polymer mixture of a thermoplastic or thermo-curing polymer base material and an amphiphilic block copolymer, e.g., as disclosed in WO 2011/051439 filed Oct. 29, 2010, the entirety of which is incorporated by reference herein. In some embodiments, the catheter tube is coated with the polymer mixture of a thermoplastic or thermos-curing polymer base material and amphiphilic block copolymer, e.g., as disclosed in WO 2011/051439.

The present disclosure further provides a method of wetting a catheter tube, the method comprising drawing a catheter tube through a wetting device disclosed herein, thereby wetting the catheter tube with a wetting agent. In some instances, the wetting device has at least one aperture. In some instances, the wetting device comprises at least a first and second aperture. In some instances, the methods comprise drawing the catheter tube through the wetting device by pulling one end a funnel attached to the catheter tube; and applying the wetting agent to a surface of the catheter tube when in the chamber.

Figure 2A:
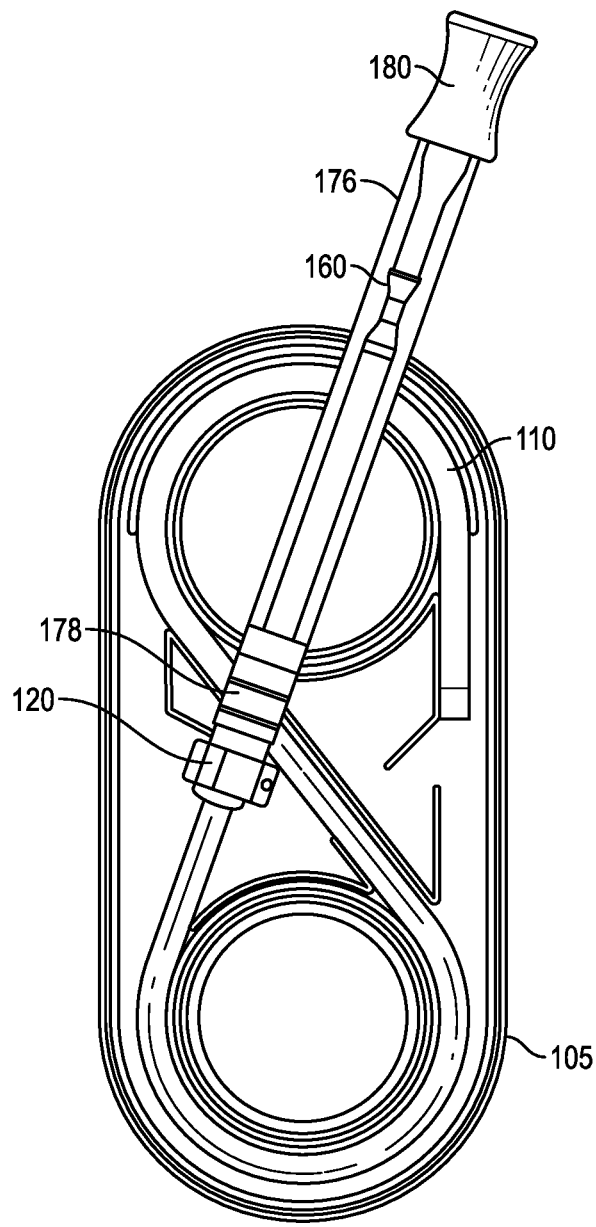
FIG. 2A shows an exemplary perspective view of the catheter package of FIG. 1 exposed upon initiation of use, and partial removal of the catheter.
Figure 2B:
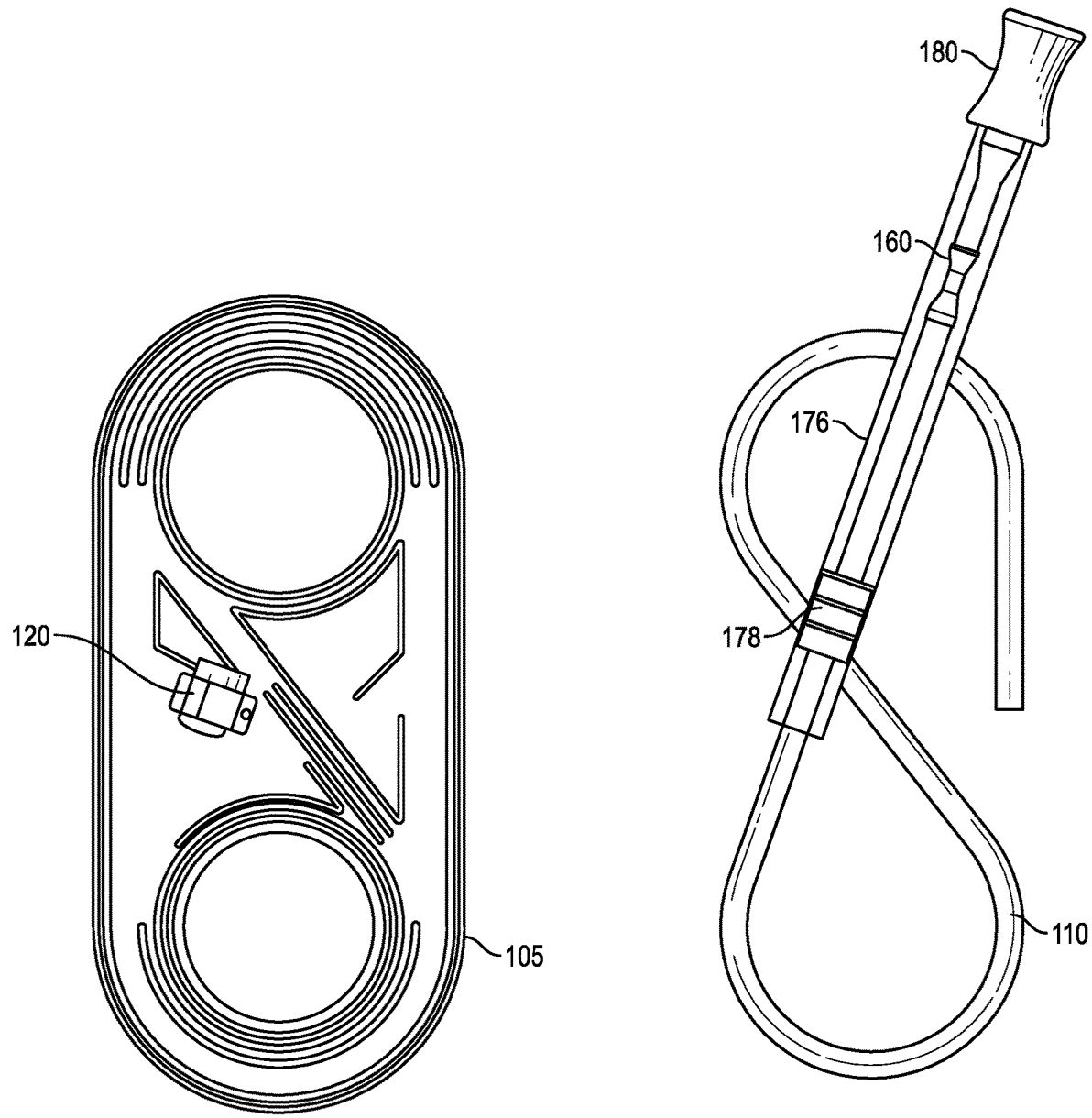
FIG. 2B shows an exemplary perspective view of the catheter package of FIGS. 1 and 2A after removal of the catheter, showing the exposed cartridge (left side) with the wetting device remaining in the cartridge. The catheter 110 is partially covered with the protective sleeve 176 and gripper 178.

Referring to the drawings and, in particular, to FIGS. 1, 2A and 2B, there is shown an intermittent catheter package generally represented by reference numeral 100.

Package 100 may have a case 102 comprising a top 103 and a bottom 105. Case 102 may have a lid 104 that seals the case. Within package 100 is a catheter tube 110 as exemplified with a urinary catheter assembly in FIG. 1. The catheter assembly may have a wetting device 120 for applying a wetting agent to catheter tube 110 during removal of the catheter from case 102. Catheter tube 110 may have an insertion end 112 that can be inserted or urged into a patient's urethra. Catheter tube 110 may have an opposite, discharge end 114. The discharge end 114 may be in fluid communication with a connector 160. The connector 160 may further be in fluid communication with a funnel 180 through which urine from the patient's bladder flows. The catheter assembly may have a handling region comprising, for example, a gripper 178 and a sleeve 176 at least partially covering the catheter tube 110 when the catheter assembly tube is removed from the case.

Typically, catheter tube 110 is unlubricated in a packaged, pre-use, or unused state. During use, catheter tube 110 is removed from the case 102 by pulling on the funnel end 180 as shown in FIG. 2A. Upon pulling of the catheter tube out of the case 102, the wetting device 120 is activated, and the catheter tube 110 is wetted upon passing of the catheter tube 110 through the wetting device 120. When the catheter tube is removed from the case 102, as shown in FIG. 2B, the wetting device 120 remains in the case 102.

Figure 3:
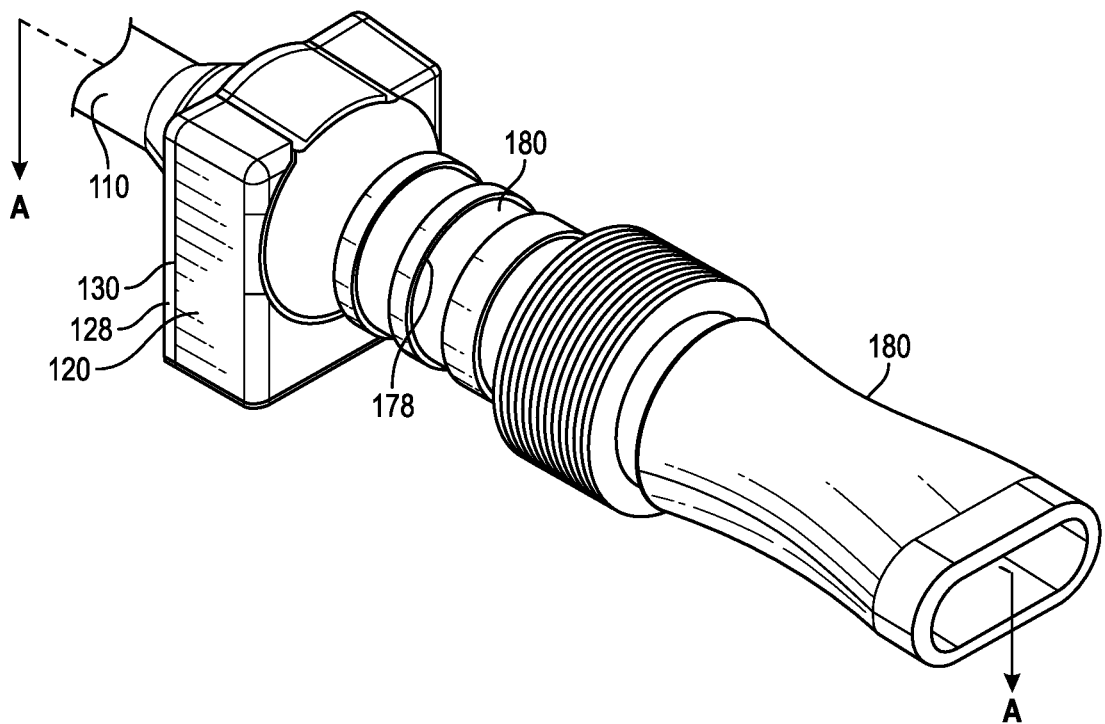
FIG. 3 shows an exemplary perspective view of a wetting device with a catheter tube therethrough.

FIG. 3 shows an isolated perspective of the wetting device 120 and funnel 180, together with the catheter tube 110 prior to use. As seen, catheter tube 110 and connector 160 threads through the wetting device 120, which includes back 130 and front 128 covers of the wetting device. Funnel 180 and gripper 178 may abut against the wetting device 120. In some embodiments connectors or other features connect or otherwise maintain a fluidic connection of the catheter tube 110 to the funnel 180, e.g., via a connector 160. As above in FIG. 2B and upon use, wetting device 120 is separated from the catheter tube 110 when the catheter tube 110 is removed from the case 102, with the wetting device 120 remaining in the case 102. In some embodiments, wetting device 120 is integral to the package. In other embodiments, wetting device 120 is removable.

As shown in FIGS. 4 to 9, the wetting device 120 is configured such that removal of a catheter tube 110 from package 100 engages the catheter and wetting device 120 to wet the catheter. The removal of catheter tube 110 may draw the catheter tube through the wetting device 120 resulting in the catheter tube being wetted on an exterior surface thereof. Note that as shown in FIG. 2B, the wetting device 120 remains in the case after removing the catheter tube 110.

Figure 4:
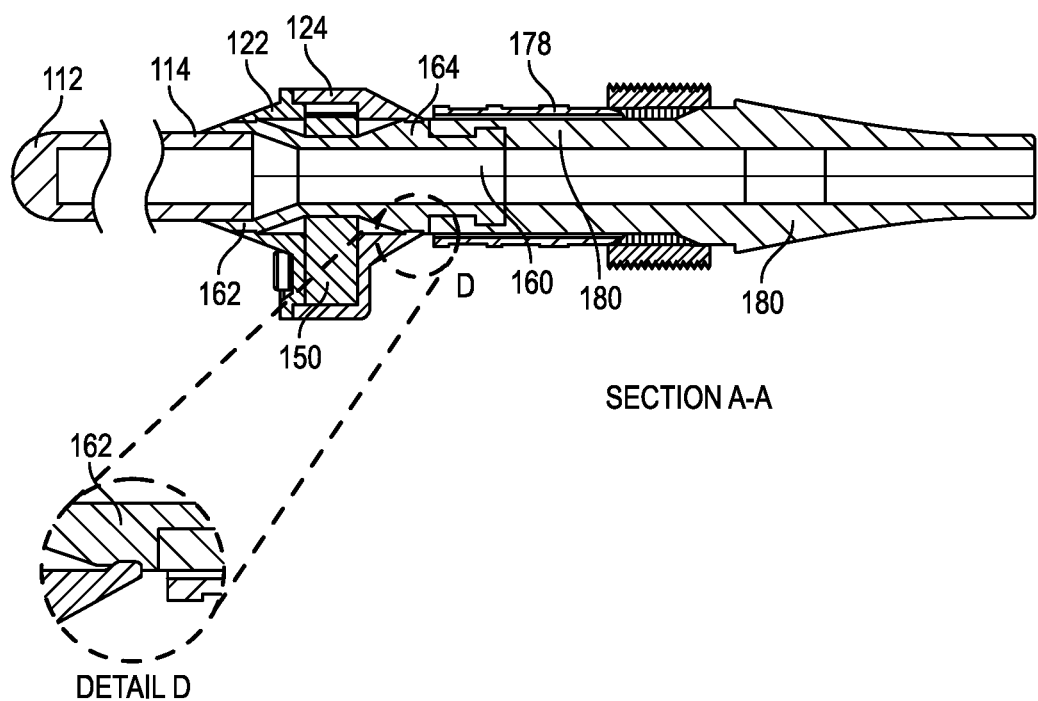
FIG. 4 shows an exemplary cross section of FIG. 3 taken along A-A.
Figure 5:
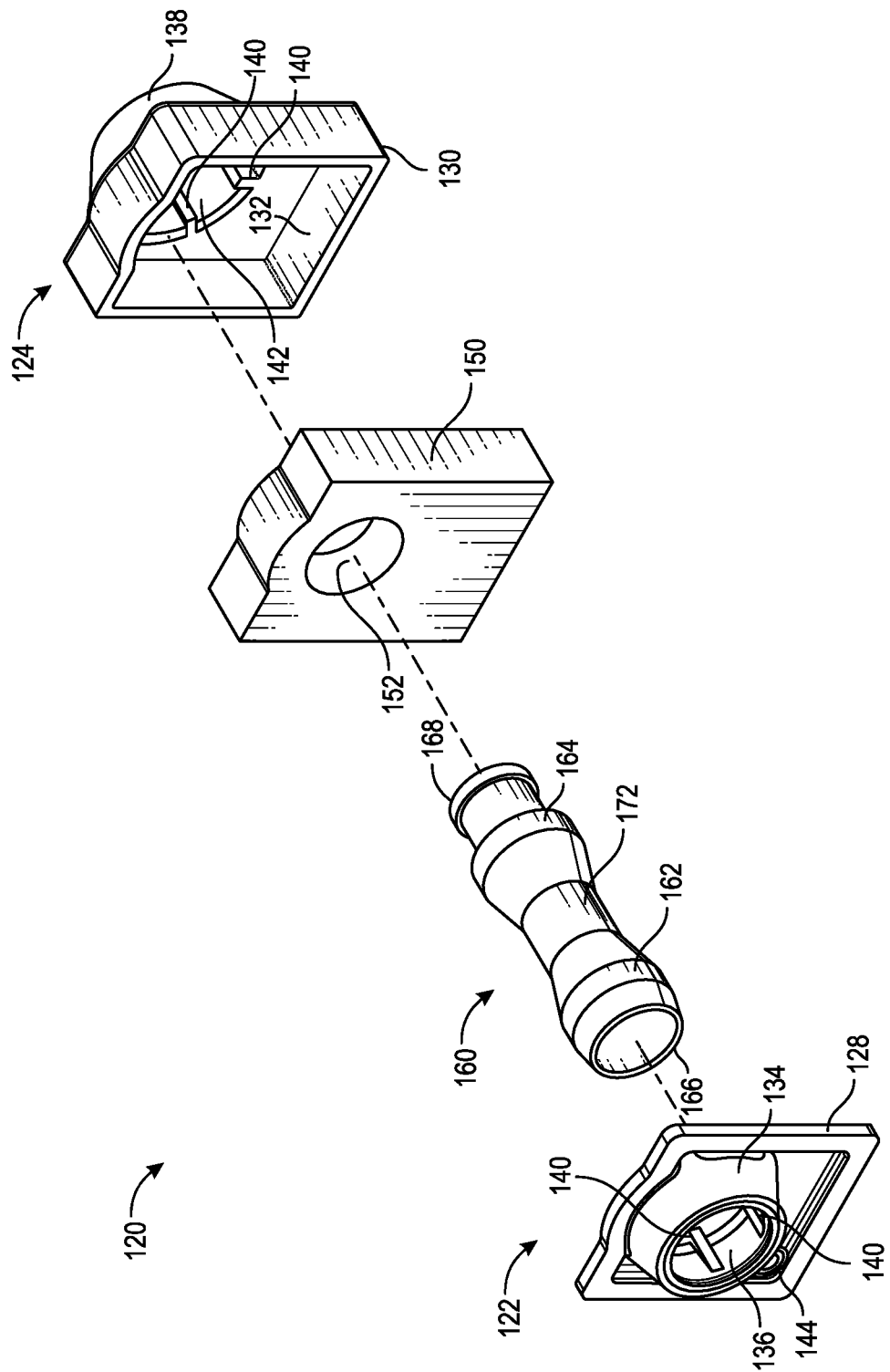
FIG. 5 shows an exemplary exploded perspective view of the wetting device of FIG. 3.
Figure 6:
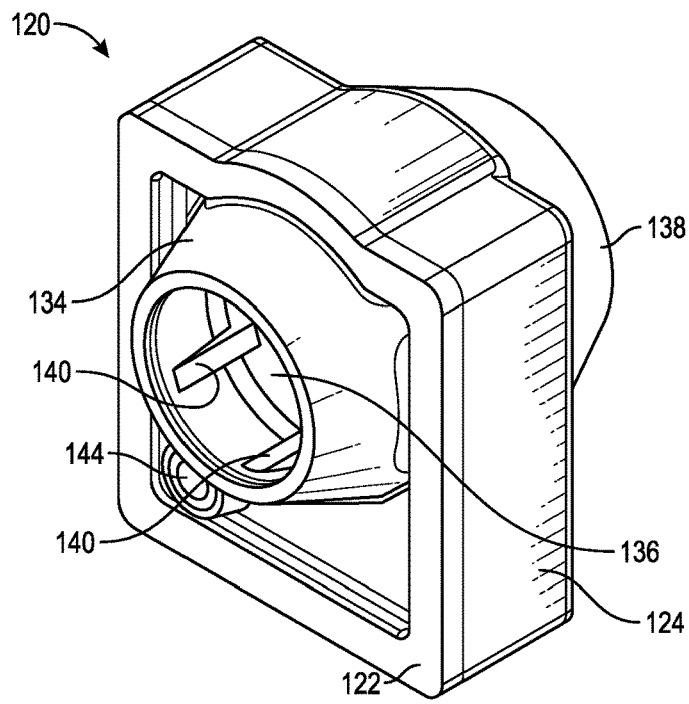
FIG. 6 shows an exemplary perspective view of the wetting device of FIG. 3.

With respect to FIGS. 3, 4 and 5, wetting device 120 may be retained in package 100 even upon removal of catheter tube 110 from the package. In some embodiments, wetting device 120 is integral to the package. In other embodiments, wetting device 120 is removable.

Wetting device 120 may comprise a chamber 126. Preferably, chamber 126 is in an enclosed structure except for at least two apertures with a hollow interior. Chamber 126 can have any geometric configuration or shape, such as, for example, rectangular, square, circular or oblong. In some embodiments, chamber 126 has wall structure such that the at least two apertures 136 and 142 are separated from each other by the hollow space.

In some embodiments, chamber 126 has a forward section 122 and a rearward section 124. Forward section 122 and rearward section 124 are joined together to form a chamber 126 therebetween. Preferably, chamber 126 and its contents are sterile. The joining of forward section 122 and rearward section 124 can be at facial surfaces 128 and 130, respectively, as shown. Preferably a surface attachment, such as, for example, an ultrasonic weld or suitable adhesive is employed to join forward section 122 and rearward section 124. In the embodiment shown, rearward section 124 has a cavity 132 formed therein. The adjectives "forward" and "rearward" describing sections 122 and 124, respectively, are not intended to imply a spatial or sequential relationship, but rather to orient the reader and facilitate understanding of the underlying principles. It should also be understood that forward section 122 and rearward section 124 can be one seamless structure.

Forward section 122 may have an elongated portion 134 with aperture 136 therethrough. Rearward section 124 may have an elongated portion 138 with aperture 142 therethrough. Thus, apertures 136 and 142 may be provided on opposing sides of chamber 126, and may be positioned in approximate axial or concentric alignment. Also, apertures 136 and 142 may be substantially circular. Embodiments without the elongated portions are envisioned.

As shown, for example, in FIG. 5, apertures 136 and 142 may be of sufficient size (e.g., diameter) to accommodate an outside outer dimension (e.g., diameter) of plug members 162 and 164 to establish a seal therebetween. Preferably, the seal is liquid tight. More preferably, the seal is fluid tight. As will be appreciated by a person ordinary skill the art, fluids are substances that continuously deform upon a tangential force acting upon a surface thereof. Fluids include gases, for example air, and liquids, for example water, aqueous mixtures, and gels.

Plug members 162 and 164 can be integral to or disposed about connector 160. In some embodiments, plug members 162 and 164 are formed from a different material than the connector. Other known methods for establishing the seal between plug members 162, 164 and apertures 136, 142 may also be suitable for use in accordance with the present disclosure.

Figure 8:
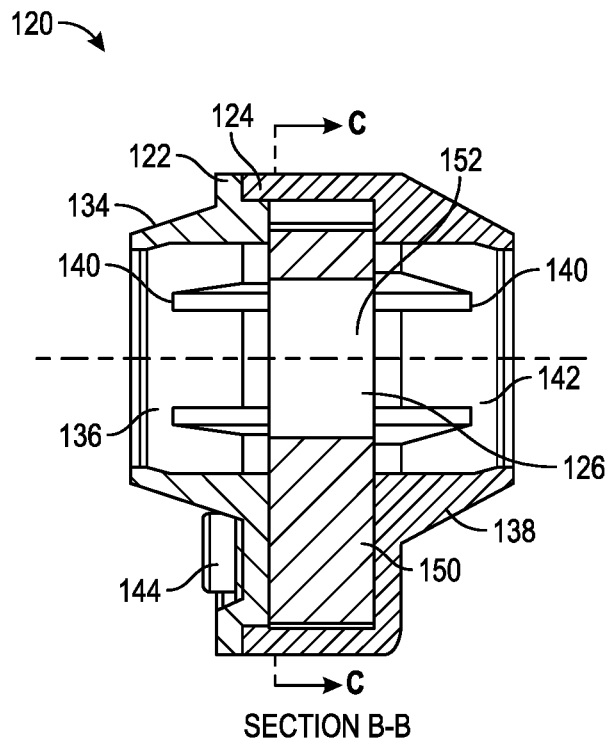
FIG. 8 shows an exemplary cross section of the wetting device taken along B-B of FIG. 7.
Figure 9:
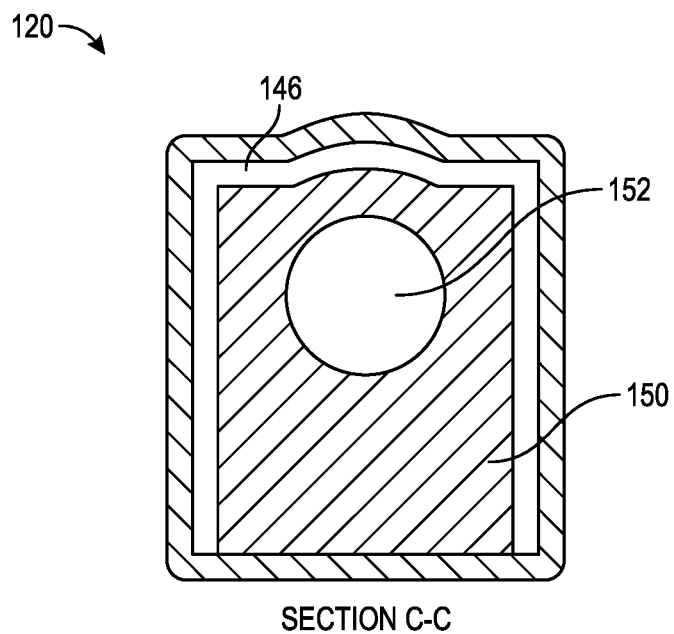
FIG. 9 shows an exemplary cross section of the wetting device taken along C-C of FIG. 8.

In some embodiments, an inner surface of aperture 136 or aperture 142 is shown to have a plurality of ribs 140 (also see FIG. 8). The plurality of ribs may be strengthening ribs. Ribs 140 can increase the rigidity of apertures 136 and 142 to resist deformation of apertures 136 and 142 and maintain the seal with plug members 162 and 164.

A compressive bias may serve to seal chamber 126 from the outside environment. In some embodiments, plug member 162 can be compressively biased against an inner surface of elongated portion 134. In some embodiments, plug member 164 can be compressively biased against an inner surface of elongated portion 138. In some embodiments, plug member 162 can be compressively biased against an inner surface of elongated portion 134, and plug member 164 can be compressively biased against an inner surface of elongated portion 138. In other embodiments, an inner surface of elongated portion 134 can be compressively biased against plug member 162 and an inner surface of elongated portion 138 can be compressively biased against plug member 164. In yet other embodiments, the compressive bias can be mutual, while in still yet other embodiments, the compressive bias can be combinations of the foregoing. It will be appreciated that in the embodiments wherein at least one of plug members 162 and 164 are formed from a different material than the connector, suitable materials for sealing can be selected without regard to longitudinal rigidity or strength.

As shown in FIG. 5, connector 160, in the packaged state, may be disposed in apertures 136 and 142.

Connector 160 may be a bored, cylindrical member. Connector 160 may span chamber 126 and apertures 136 and 142 when positioned in the catheter assembly. Connector 160 may have a first end 166 and a second end 168 with a middle section 172 therebetween. As mentioned, in the embodiment shown, connector 160 may have a plug member 162 proximate to first end 166, and a plug member 164 proximate to second end 168. Plug member 162 and plug member 164 may concurrently seal apertures 136 and 142, respectively, when catheter tube 110 is in the unused or packaged state. In such embodiments, when apertures 136 and 142 are sealed, chamber 126 may be liquid tight. In some embodiments, when apertures 136 and 142 are sealed, chamber 126 may be fluid tight so that leaks in package 100 are inhibited.

Catheter tube 110 may connect to connector 160 at the first end 166 thereof. Funnel 180 may connect to second end 168 of connector 160. In such configuration, connector 160 can provide liquid or fluid tight communication between catheter tube 110 and funnel 180. In some instances, an inner diameter of connector 160 is greater than or equal to an inner diameter of catheter tube 110. A larger inner diameter may prevent impingement of urinary discharge or flow. A larger inner diameter may minimize pressure buildup.

As discussed above, plug members 162 and 164 can be compressively biased against elongated portions 134 and 138, respectively, to seal chamber 126 from an outside environment. In some instances, this sealing aspect is important to allow wetting device 120 to function. In some instances, this sealing aspect is important to allow wetting device 120 to wet catheter tube 110 upon its removal from package 100. In some instances, this sealing aspect is important to prevent wetting agent from drying out. In some instances, this sealing aspect is important to prevent wetting agent from leaking out of chamber 126 and into package 100. Connector 160 is preferably made of a material having a good moisture barrier for reasons appreciated by those of skill in the art. For example, a preferred material for connector 160 is HDPE because it has a low MVTR.

Referring to wetting device 120, a wetting applicator 150 may be disposed in chamber 126 around connector 160. Wetting applicator 150 may be an element that retains fluid and permits the fluid to be applied to catheter tube 110 as the catheter tube touches the element. Wetting applicator 150 can be made of a flexible or resilient material that can absorb or retain liquid, lubricant or the like (hereinafter collectively called "lubricant"), and permit application of the lubricant upon contact by a tube to the wetting applicator 150. A non-limiting example of a flexible or resilient material is foam. Foam may be described as a substance formed of varying compressible cell structures and pockets of air. Wetting applicator 150 can also be, but is not limited to, an absorbent pad, a sponge, a gel matrix, and a liquid capsule. The wetting device 120 may have a space 146 between the wetting applicator 150 and an inner surface of an enclosure of the wetting device 120, as exemplified in FIG. 9.

Wetting applicator 150 may have an opening 152 therethrough (see also FIG. 9) through which connector 160 is disposed. Opening 152 may be sized to apply or transfer lubricant from wetting applicator 150 to catheter tube 110. It will be appreciated that opening 152 can be smaller in size than wetting device apertures 136 and 142. In some instances, opening 152 is similar in size (e.g., an inner diameter to an outer diameter) to middle section 172. In some instances, the outer diameter of middle section 172 may be substantially similar or slightly smaller in size than that of catheter tube 110. In some instances, the outer diameter of middle section 172 may be about 0.01% to about 10% smaller in size than that of catheter tube 110. In some instances, the outer diameter of middle section 172 may be about 0.01% to about 1% smaller in size than that of catheter tube 110. This configuration may prevent wetting applicator 150 from being compressed prior to use. This configuration may also promote contact between substantially the entire length of catheter tube 110 and wetting applicator 150.

Opening 152 can be an aperture, a slit or plurality of slits. In some embodiments, the plurality of slits can form an asterisk, star or similar shaped cross-section.

In some instances, a port 144 can be located on or in chamber 126, such as in forward section 122, for introducing fluid, lubricant or other suitable material into chamber 126. This introduction of fluid may be used to load wetting applicator 150 with a wetting agent. Although shown in FIGS. 5-7 on a forward face of forward section 122, port 144 can be disposed through or in other surfaces of wetting device 120 depending on the package for the wetting device, see, e.g., FIGS. 13, 14 and 16. In some instances, port 144 comprises a one-way valve to only permit flow into chamber 126. In some instances, wetting applicator 150 is pre-loaded with a wetting agent. In some instances, the wetting applicator is pre-loaded with a first wetting agent and is capable of receiving a second wetting agent or other agent through the port.

As assembled, aperture opening 152 may be aligned with apertures 136 and 142, such that an unwetted catheter tube 110 first passes through aperture 136, and then, is drawn through opening 152 where wetting agent, absorbed or contained in wetting applicator 150, is transferred to the exterior surface of catheter tube 110 to wet the exterior surface along the length of the catheter tube. In this example, the catheter tube may now be suitably wetted and exits wetting device 120 through aperture 142, which may remove undesired or excess wetting agent so that the catheter tube is ready for use. In such orientation, discharge end 114 is wetted before insertion end 112. Detail D shows how apertures 136 and 142 creating a seal against the plug sections 162 and 164 of connector 160. The interference fit between these parts must be sufficiently tight to prevent leakage of water over the life of the device.

Figure 10:
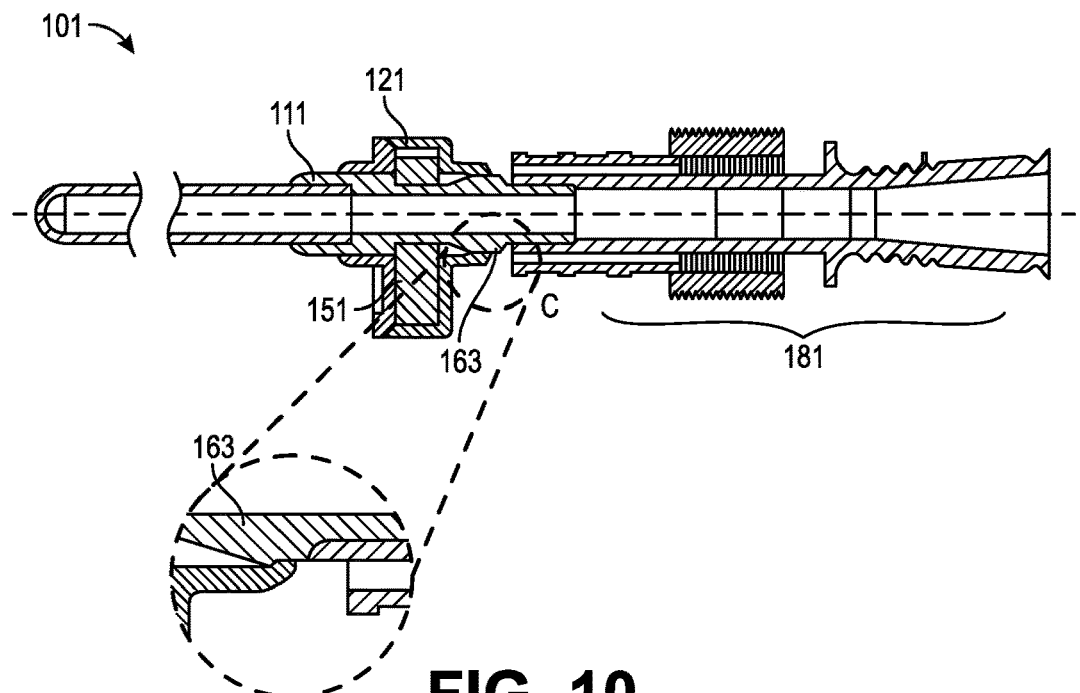
FIG. 10 shows an exemplary cross section of a catheter assembly including a wetting device.

Referring to FIG. 10, catheter assembly 101 may comprise wetting device 121, wetting device applicator 151, and connector 111. The catheter assembly may also comprise handling region 181 comprising a gripper, funnel and expandable sleeve. Region C provides additional detail of the plug section of wetting device 121 sealing against plug sections 163 and 165 when in a stored state.

Figure 7:
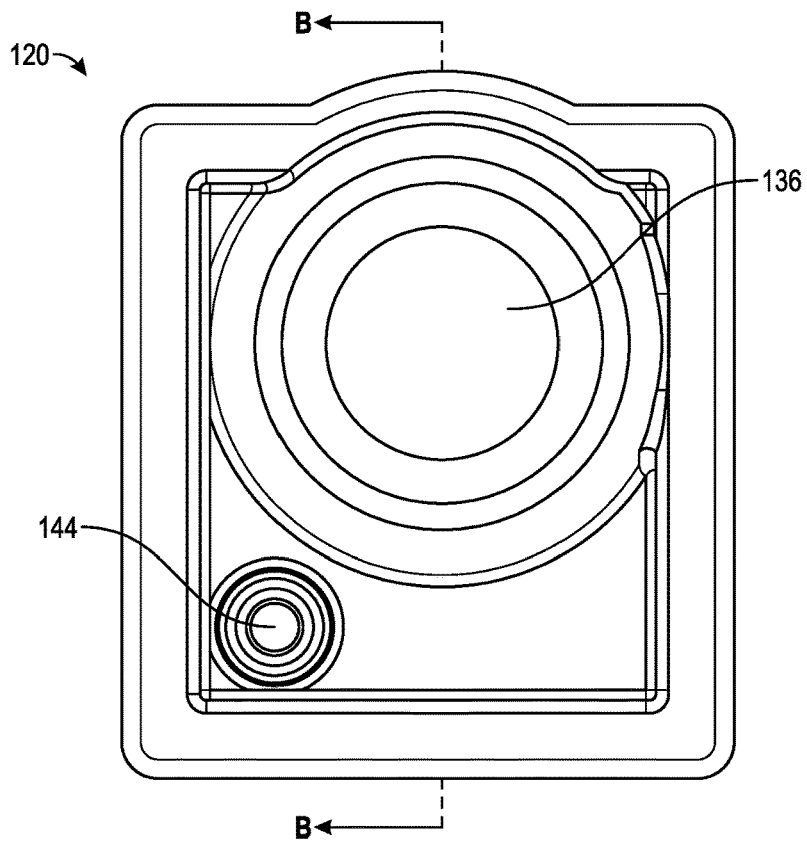
FIG. 7 shows an exemplary end view of the wetting device of FIG. 3.
Figure 11:
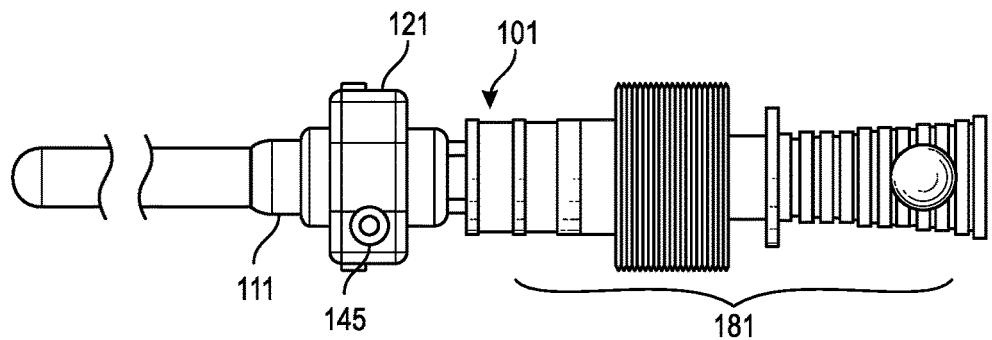
FIG. 11 shows an exemplary outer view of a catheter assembly including a wetting device.
Figure 12:
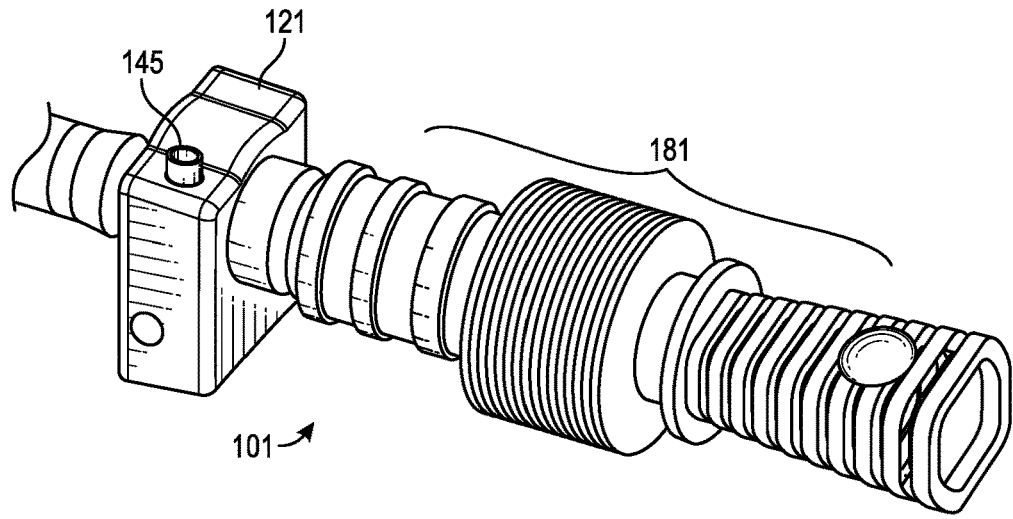
FIG. 12 shows an exemplary cross section of a catheter assembly including a wetting device.

FIG. 11 and FIG. 12 may represent an outside view and perspective view, respectively, of the catheter assembly shown in FIG. 10, as viewed from a top assembly of a case. This side of the catheter assembly may be referred to as the "top" of the catheter assembly, and the top of its respective parts. Catheter assembly 101 may comprise wetting device 121 and connector 111. The catheter assembly may also comprise handling region 181 comprising a gripper, funnel and expandable sleeve. Port or filling hole 145 may be present on wetting device 121 to permit wetting agent into wetting device 121 and in contact with a wetting applicator (151 in FIG. 10). As shown in FIG. 11, the port may be present on the top of the wetting device, as opposed to an end (also referred to as forward section and rearward section) of a wetting device as shown in FIG. 7. FIG. 11 shows an embodiment including a compressed or concertina fold sleeve located over the handling region and funnel, which can be extended during removal of the catheter from the wetting device 121, which in turn sits in catheter packaging or case 102 (see, e.g., FIGS. 1 and 2, supra).

Figure 13:
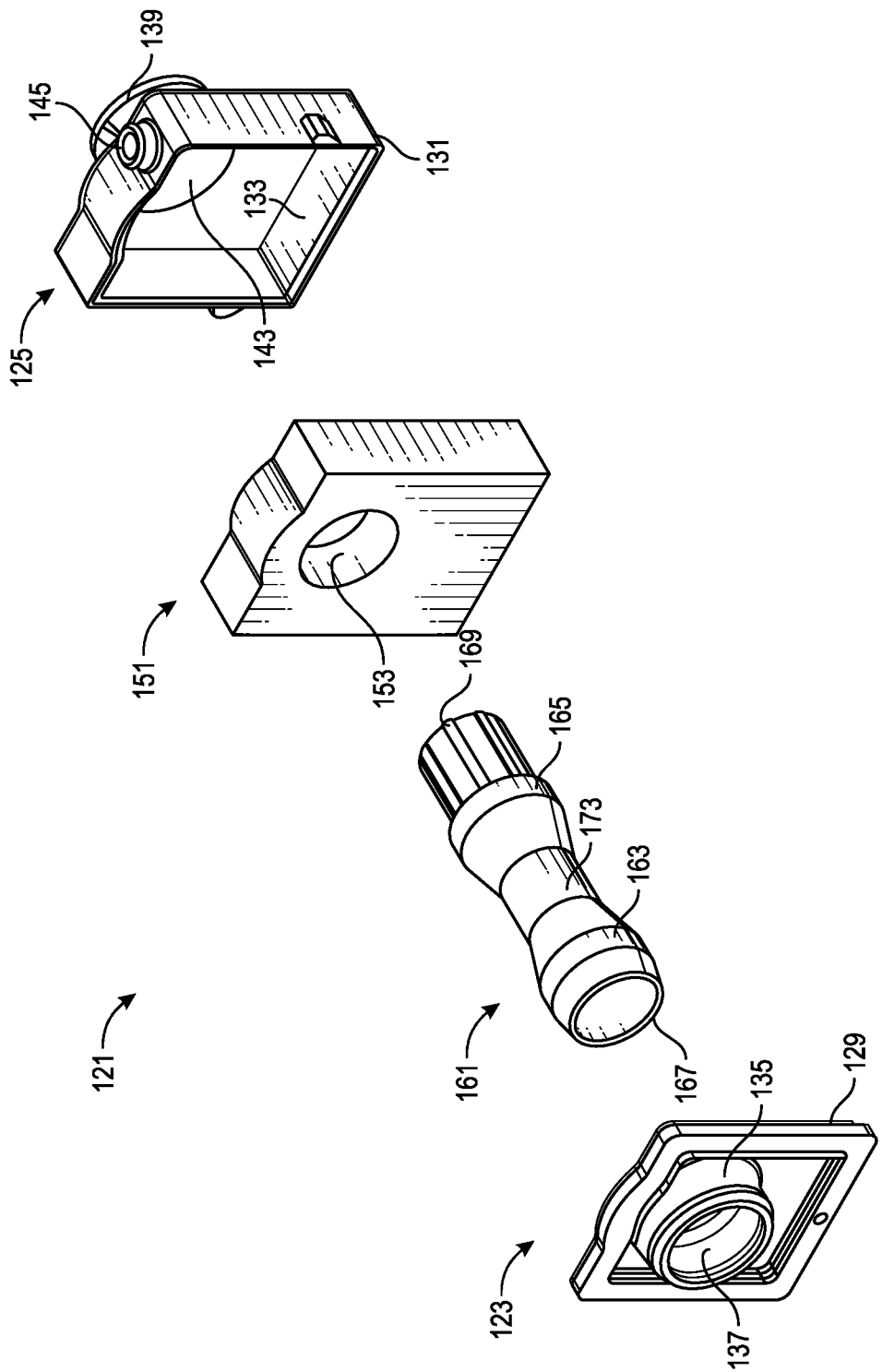
FIG. 13 shows an exemplary exploded perspective view of the wetting device of FIG. 10.

FIG. 13 may represent an exploded view of the wetting device 121 of catheter assembly 101 shown in any one of FIGS. 10-12. Forward section 123 may have aperture 137, elongated portion 135, and facial surface 129. Rearward section 125 may have aperture 143, port 145, cavity 133, facial surface 131 and elongated portion 139. Connector 161 fits through opening 153 of wetting applicator 151. Connector 161 comprises first end 167 and second end 169, a middle section 173 and plug members 163 and 165. Middle section 173 may have a smaller circumference than then plug members, such that when assembled and before use, middle section 173 rests within opening 153 without applying any pressure to wetting applicator 151. When the catheter tube is deployed and pulled through opening 153, at least one of the plug members 163 and 165, pass through opening 153, applying pressure to wetting applicator 151, thereby squeezing wetting agent out of the wetting applicator and on to the following catheter tube.

Figure 14:
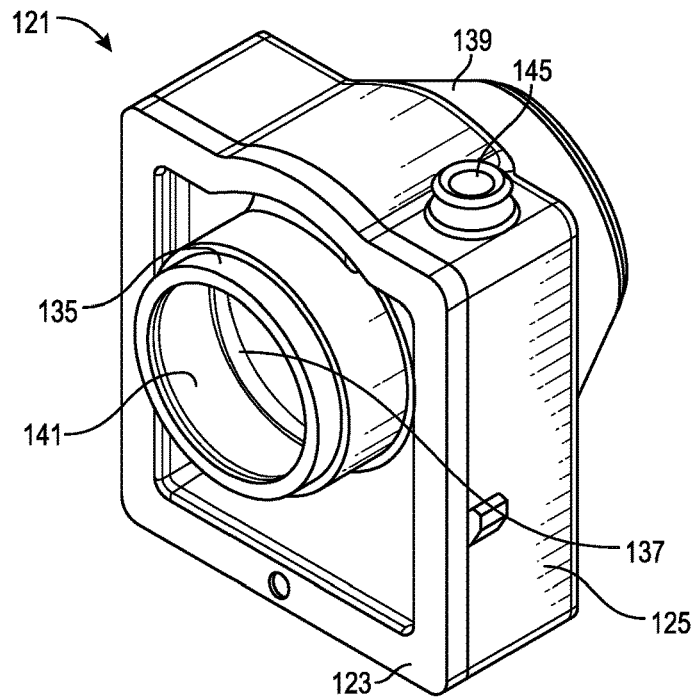
FIG. 14 shows an exemplary (non-exploded) perspective view of the wetting device of FIG. 10.
Figure 15:
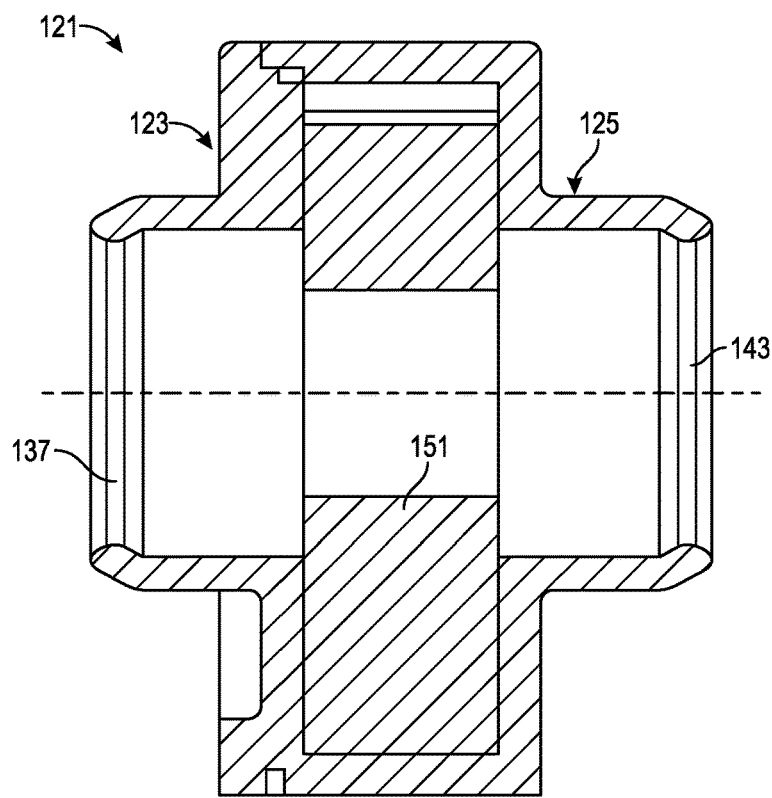
FIG. 15 shows an exemplary side view of the wetting device depicted in FIG. 14.
Figure 16:
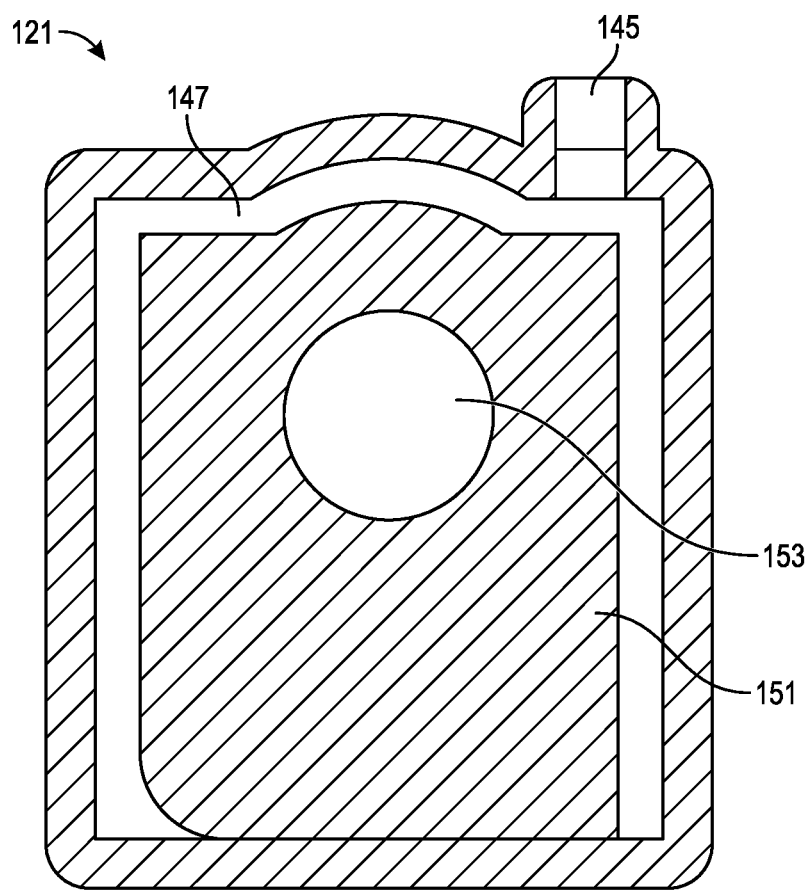
FIG. 16 shows an exemplary end view of the wetting device depicted in FIG. 14.
Figure 17:
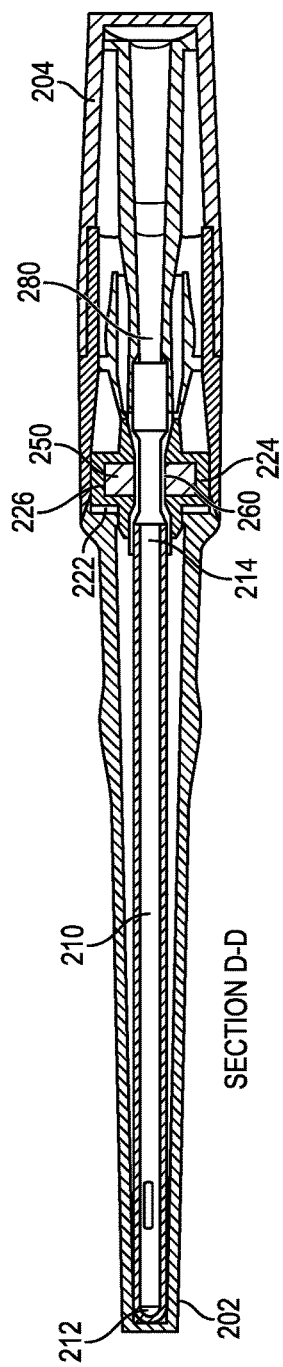
FIG. 17 shows an exemplary cross section view of a catheter assembly with a wetting device.
Figure 18:
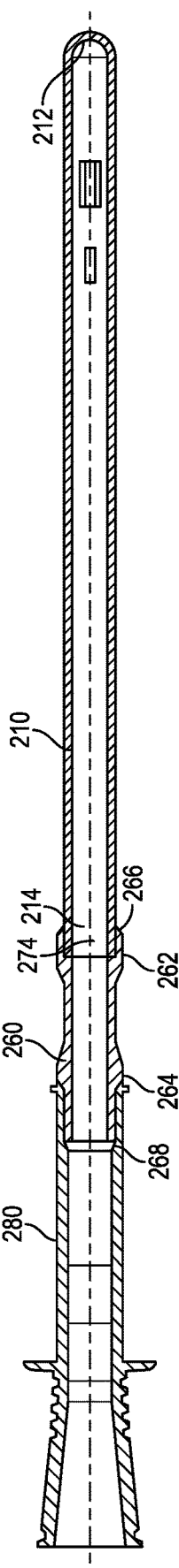
FIG. 18 shows an exemplary cross section view of a catheter assembly with a wetting device.
Figure 19:
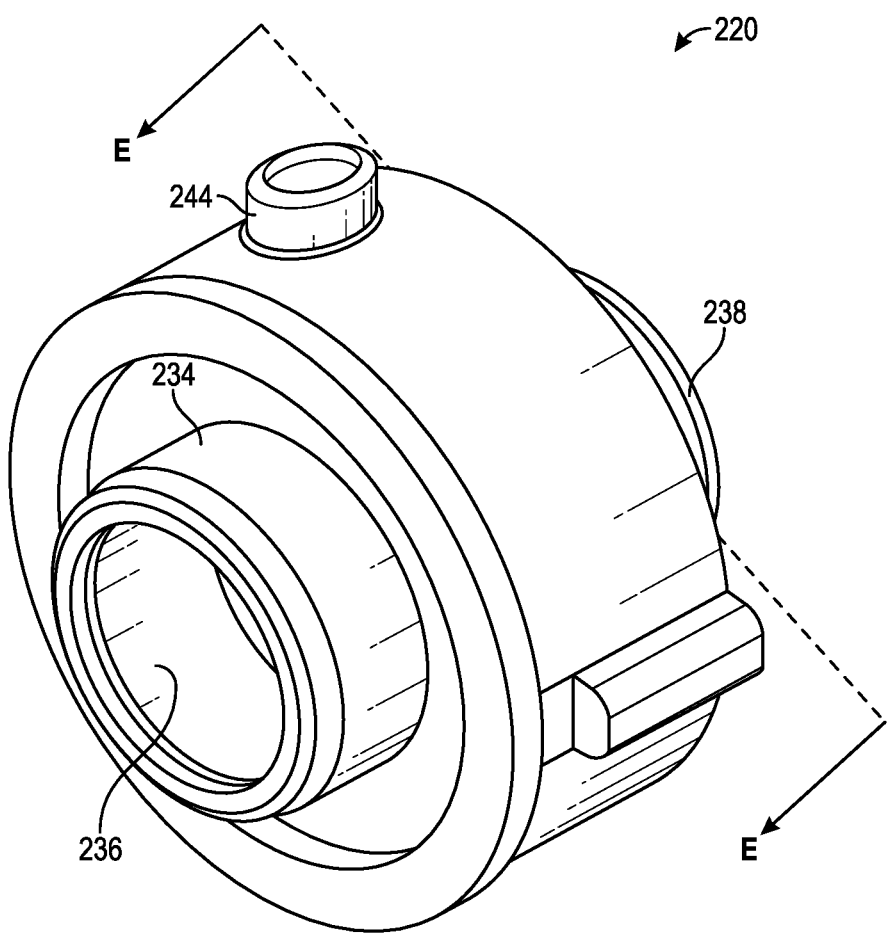
FIG. 19 shows an exemplary perspective view of a wetting device.
Figure 20:
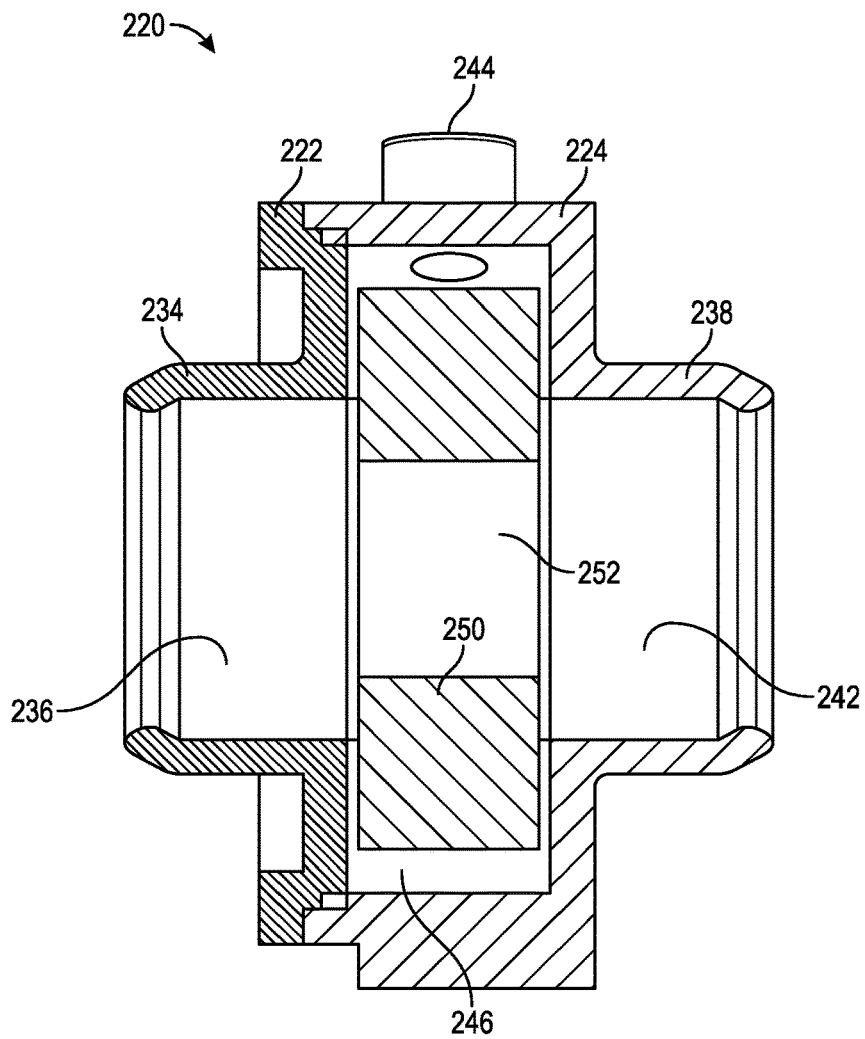
FIG. 20 shows an exemplary cross section view along E-E of FIG. 19.
Figure 21:
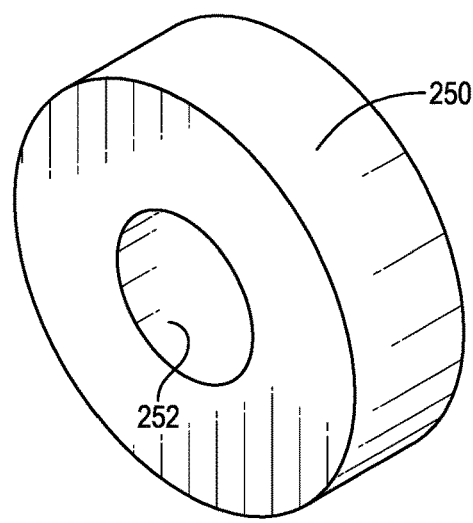
FIG. 21 shows an exemplary perspective view of a wetting applicator of a wetting device.
Figure 22:
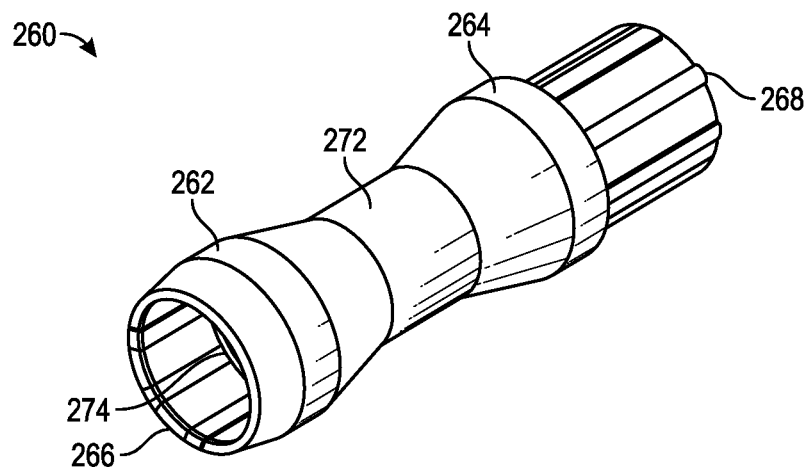
FIG. 22 shows an exemplary perspective view of a connector of a wetting device.

FIGS. 14-16 may show additional views of the wetting device 121 shown in FIG. 13. FIG. 14 shows a (non-exploded) perspective view with elongated portions 141 and 139 on forward section 123 and rearward section 125, respectively. FIG. 15 shows a cross-section from a side view of the wetting device 121 in FIG. 14, with wetting applicator 151, forward section 123 having aperture 137, and rearward section 125 having aperture 143. FIG. 16 shows a cross-section of an end view of the wetting device 121 with wetting applicator 151 having opening 153, and port 145. Feature 147 indicates a space between the wetting applicator 151 and an inner surface of an enclosure of the wetting device 121, as described herein.

Referring to FIGS. 17-20, catheter tube 210 may have an insertion end 212 that is insertable into a patient's urethra and a discharge end 214 in fluid communication with a connector 260 and a funnel 280 through which urine from the patient's bladder flows. Catheter tube 210 may be dry or unlubricated in a packaged state. Removal of catheter tube 210 from package 200 may actuate wetting device 220. As catheter tube 210 is drawn through wetting device 220, a wetting agent may be applied to an exterior surface of the catheter tube. As with the first embodiment, wetting device 220 may be in package 200 and can be retained in the package when catheter tube 210 is removed. Alternatively, wetting device 220 can be integral to package 200. Wetting device 220 may have a forward section 222 and a rearward section 224 that together form a chamber 226 therebetween. In the exemplary embodiment shown, forward section 222 has a protruding member 234 with aperture 236 therethrough. Rearward section 224 may have a protruding member 238 with aperture 242 therethrough. These outward protruding members 234, 238 may create additional volume in chamber 226 and, as such, the depths are accordingly sized. Further, there may be two aligned apertures 236, 242, preferably axially aligned, disposed at opposing ends of chamber 226. The catheter assembly shown is stored within case body 202, and removable through an opening (not shown) beneath lid 204.

As exemplified in FIGS. 18-22, wetting devices disclosed herein may be configured to be used with a catheter tube, wherein the catheter tube is attached to or connected to a connector. By way of non-limiting example, the connector may connect the catheter tube to a funnel. In some instances, the connector 260 spans chamber 226. In some cases, the connector plugs at least one of apertures 236 and 242 in a packaged or unused state. Like connector 160, connector 260 can have a middle section 272 between a first end 266 and a second end 268. Connector 260 can have a plug member 262 proximate to first end 266, and a plug member 264 proximate to second end 268. Plug member 262 and plug member 264 can concurrently seal apertures 236 and 242, respectively. Displacement of connector 260 unseals apertures 236 and 242.

In some instances, catheter tube 210 connects to first end 266 of connector 260. See, e.g., FIG. 18. In some embodiments, catheter tube 210 is positioned in a counterbore 274, where it is press fit or sonic welded. Funnel 280 may connect to and fit around a second end 268 of connector 260. Again, a press fit or sonic weld can be used. Such a configuration, namely where catheter tube 210 fits into connector 260 and connector 260 fits into funnel 280, may ensure that there is no pressure buildup due to cross sectional flow constriction.

Wetting applicator 250, like wetting applicator 150, may have an opening 252 therethrough. Wetting applicator 250 may be disposed in chamber 226 with connector 260 disposed in opening 252. In some instances, wetting applicator 250 is compressible. In some instances, wetting applicator 250 is liquid impregnable. In some instances, wetting applicator 250 is sized to apply liquid to catheter tube 210. In some instances, wetting applicator 250 is sized, in a dry state, so that there is space 246 between the outer circumference of the wetting applicator and an inner diameter of chamber 226 to allow the wetting applicator to move and provide space for expansion of the wetting applicator.

As shown, a port 244 may be located through a top wall on rearward section 224. Port 244 is for filling chamber 226 with lubricant to load wetting applicator 250. It will be appreciated that port 244 can be disposed in or through other surfaces of wetting device 220 depending on the package for the wetting device. Port 244 can be a one-way port to prevent leakage.

In an assembled state, apertures, 236 and 242 may be in concentric alignment with connector 260 and opening 252.

In other embodiments, apertures, 236 and 242 are not in concentric alignment with connector 260 and opening 252. In use, connector 260 may be displaced, thus breaking the seal at apertures 236 and 242. A dry catheter tube 210 may be first drawn through aperture 236 into chamber 226. Next, catheter tube 210 may be drawn through opening 252 where a wetting agent in wetting applicator 250 is applied to an exterior, such as the outer or exterior surface, of catheter tube 210. The catheter tube 210, now lubricated, may be drawn out of chamber 226 through aperture 242 (that removes excess lubricant) and is ready for use by a patient.

Figure 23:
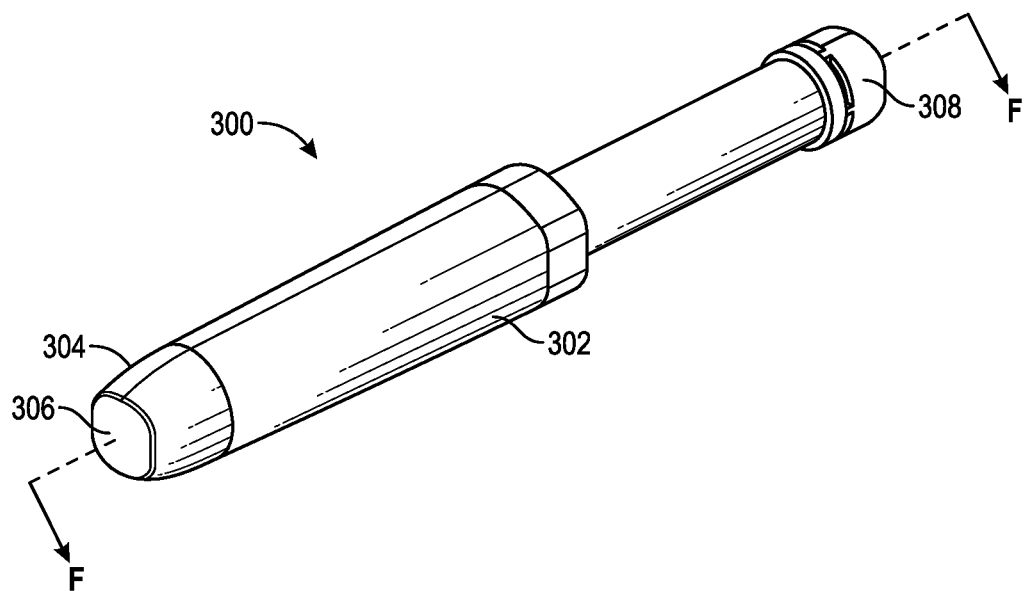
FIG. 23 shows an exemplary perspective view of a catheter package having a wetting device according to the present disclosure in a packaged state.
Figure 24:
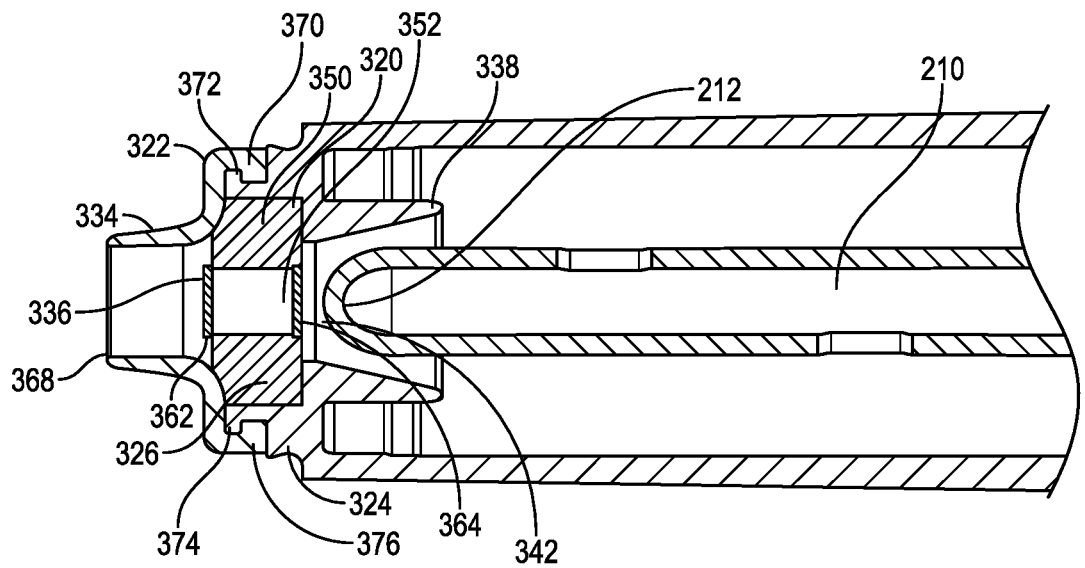
FIG. 24 shows an exemplary partial cross section view of FIG. 23 taken along line F-F showing the wetting device.
Figure 25:
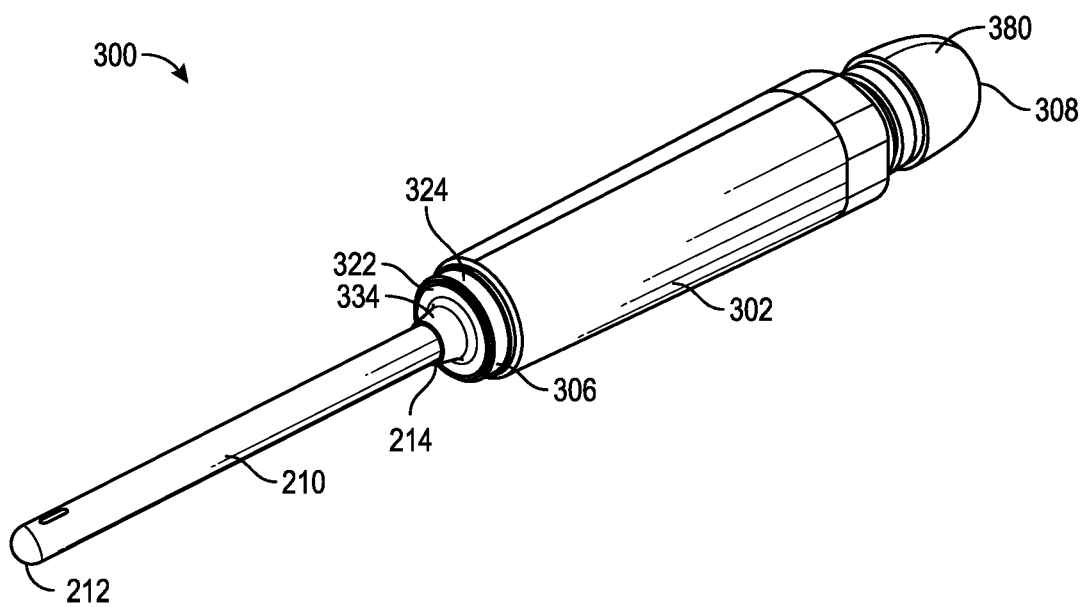
FIG. 25 shows an exemplary view of the package of FIG. 23 shown with the catheter actuated in a ready for use, or wetted state.

Referring to FIGS. 23 to 25, a third exemplary embodiment of a wetting device 320 of the present disclosure is shown. In this example, wetting device 320 is disposed in a package 300.

Package 300 has a body 302 and a removable cap 304. Body 302 has a proximal end 306 and a distal end 308 that is opposite the proximal end. Cap 304 is connected and, preferably, affixed to a proximal end 306.

Package 300 is unlike packages 100 and 200 in that catheter tube 210 is not removable therefrom. Rather, catheter tube 210 is integral with the package. Further, catheter tube 210 is in fluid communication with a discharge opening 380 at distal end 308. Body 302 has an actuation mechanism, such as a plunger (not shown), to push catheter tube 210 through wetting device 320. At the same time, or in a sequence, the actuation mechanism can open discharge opening 380. Accordingly, unlike wetting devices 120 and 220, wetting device 320 lubricates catheter tube 210 from insertion end 212 to discharge end 214.

As shown in FIG. 24, wetting device 320 may have a forward section 322 and rearward section 324. A chamber 326 may be formed between forward section 322 and rearward section 324. Chamber 326 may contain a wetting applicator 350 that has an opening 352 therethrough. As shown, wetting applicator 350 may be cylindrical and generally conforms to the shape of body 302. It should be noted that wetting applicator 350 will, preferably, conform to the shape of body 302 so that if body 302 has a different shape, such as oblong, wetting applicator 350 will adapt to that shape.

Chamber 326 may have an aperture 336 through forward section 322 and aperture 342 through rearward section 324. These apertures 336, 342 may be disposed in concentric alignment with catheter tube 210 so that the catheter can be pushed through chamber 326 along a central axis thereof.

FIG. 24 shows a side view of a cross-section of a package 300. On the left, the package 300 is shown with cap 304 (not shown) removed to expose the locator tip 334. Locator tip 334 may be described as tapered, with a slope that may gradually increase to the base of the locator tip. Locator tip 334 may be described as cone shaped. Although hollow, the locator tip 334 may be described as having a flat end. Locator tip 334 may be described as having a blunt end. The locator tip end has a diameter that is smaller than the base of the locator tip where it is attached to the device housing. A cross-sectional side view depicts the catheter tube 210 protected from exposure by the locator tip 334. In addition, in this exemplary case, the catheter tube 210 must be pushed through a wetting device 320 and the locator tip 334 before it will make contact with tissue. The locator tip 334 may have a tapered region near the locator tip opening 368. FIG. 24 further shows housing lip 372, 374 and a locator tip ring 370, 376 that attach the locator tip to the body.

Chamber 326 may be sealed in a packaged or pre-use state by plug member 362 at forward section 322 and by a plug member 364 at rearward section 324. Plug members 362 and 364 may be made of a material pierceable by catheter tube 210. Such materials are, but are not limited to, a metal foil and plastic foil such as polyethylene (PE) or polypropylene (PP) or a coated paper. Plug members 362 and 364 can have features such as perforations, indentations, weakened areas, and the like that facilitate piercing. Plug members 362 and 364 are preferably the same size and shape.

Alternatively, it is envisioned that a chamber, like chamber 226, can be used and apertures 236 and 242 are sealed by a plug member incorporated in the inside of cap 304.

Rearward section 324 can also have an extension, namely extension 338. Extension 338 is a cylindrical protrusion having a conical aperture therethrough that decreases in diameter towards chamber 326. Advantageously, extension 338 facilitates pushing catheter tube 210 out of package by funneling catheter tube 210 towards a central axis of apertures 336 and 342.

As shown in FIG. 25, catheter tube 210 has been pushed through chamber 326 and proximal end 306, and thus is now lubricated and in use. Not shown is the urethra into which catheter tube 210 has been inserted. When catheter tube 210 is pushed through chamber 326, the actuation mechanism also creates discharge opening 380 at distal end 308. Catheter tube 210 is in fluid communication with discharge opening 380.

In an alternative embodiment, body 302 can be made from a soft flexible material capable of collapsing in a concertina fashion such as bellows to push the catheter tube 210 through wetting device 320.

Figure 26:
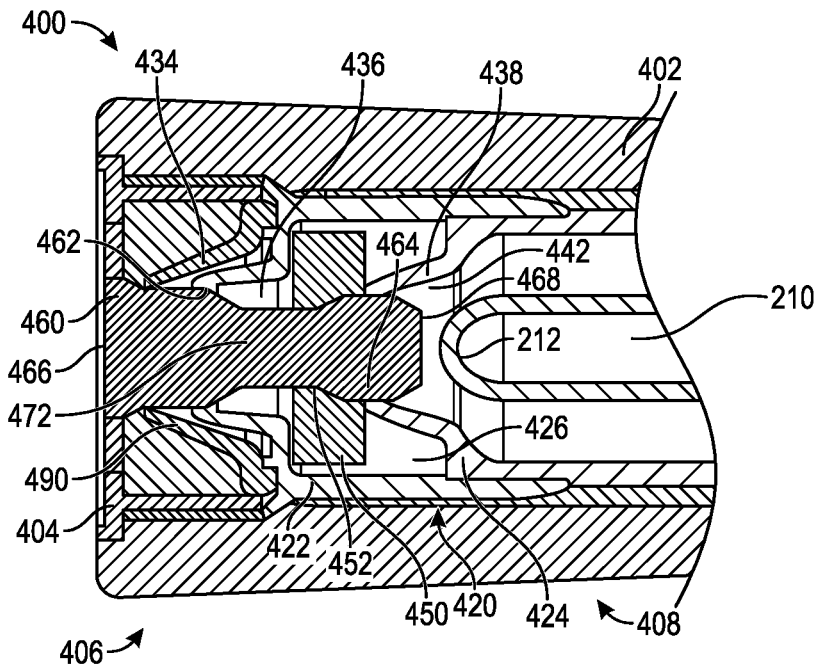
FIG. 26 shows an exemplary partial cross section view of an exemplary wetting device according to present disclosure.

Referring to FIG. 26, a fourth exemplary embodiment of a wetting device 420 according to the present disclosure is shown. Wetting device 420 is disposed in package 400.

Package 400 has a locator tip 490, and body 402 in which a chamber 426 of wetting device may be retained and a cap 404 that may be disposed at a proximal end 406 of the package to close the package. A plug 460 for sealing wetting device 420 is joined or integral to cap 404.

Unlike the first, second, and third embodiments discussed above, catheter tube 210 may be not affixed to a connector or plug. In this fourth embodiment, catheter tube 210 may be coupled to an actuator (not shown) which pushes the catheter tube linearly in a direction from distal end 408 to proximal end 406 and through wetting device 420. Catheter tube 210 is dry or unwetted prior to being pushed through wetting device 420, such as in a packaged state.

Chamber 426 of wetting device 420 may be formed between a forward section 422 and a rearward section 424. Two aligned apertures 436, 442, in some instances, axially aligned, are disposed at opposing ends of chamber 426, such as aperture 436 through forward section 422 and aperture 442 through rearward section 424. In preferred embodiments, forward section 422 has an elongated portion 434 through which aperture 436 may be disposed. Rearward section may have an elongated portion 438 through which aperture 442 is disposed.

Elongated portions 434, 438 may be conical shaped extensions of forward and rearward sections 422 and 424, respectively. Elongated portion 434 may extend away from chamber 426, while elongated portion 438 extends into chamber 426. An inner diameter of each of elongated portions 434, 438 may decrease in a direction from distal end 408 to proximal end 406. Rearward section 424 also may form a tubular shell around catheter tube 210 in a direction away from chamber 426. Such a configuration may serve to protect an outer surface of catheter tube 210 from contamination. This configuration may further facilitate movement of catheter tube 210. For instance, this configuration may guide or assist the catheter tube through aperture 442 into chamber 426 and then through aperture 436 out of chamber 426.

As discussed above, plug 460 may be affixed or directly affixed to cap 404 and seals chamber 426. Thus, upon removal of cap 404, plug 460 may also be removed from chamber 426, thereby creating a volume to allow catheter tube 210 to be pushed through.

Plug 460 may have a plug member 462 proximate to first end 466, and a plug member 464 proximate to second end 468, with a center 472. Plug member 462, 464 may concurrently seal chamber 426, preferably at apertures 436 and 442, respectively. Plug 460 may be made of a material having a moisture barrier such as HDPE or PP.

A wetting applicator 450, similar to wetting applicator 150, 250, 350, may be disposed in chamber 426 and may function in a substantially similar manner. Wetting agent 450 may have an opening 452 through which catheter tube 210 passes, and preferably contacts, as it is wetted by the wetting applicator.

Referring to FIGS. 27 through 33, wetting devices disclosed herein may be useful in catheter assemblies intended for insertion of a catheter tube into a female urethra. While FIGS. 27 through 33 are illustrative of wetting devices in such catheter assemblies, it is understood that some features and configurations depicted in these figures would be suitable for catheter assemblies intended for insertion of a catheter tube into a male urethra as well.

Figure 27:
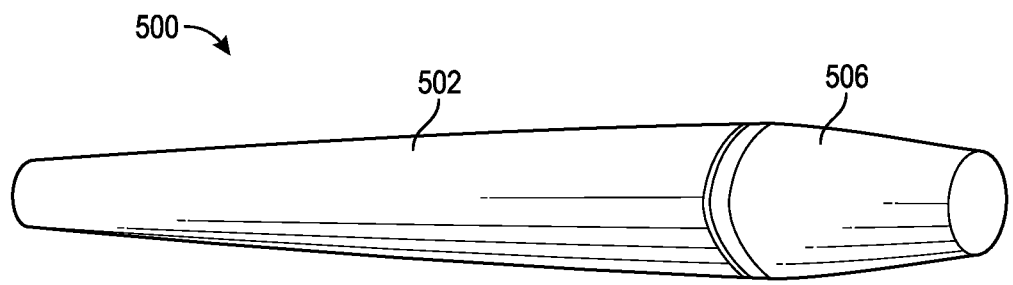
FIG. 27 shows an external view of an exemplary female catheter assembly that may contain a wetting device disclosed herein.

FIG. 27 shows a female catheter assembly 500, comprising housing 502 and cap 506. Wetting device and wetting applicator (not shown) are contained within the housing 502. Note that the wetting device contained inside is sized appropriately for such a compact catheter assembly.

Figure 28:
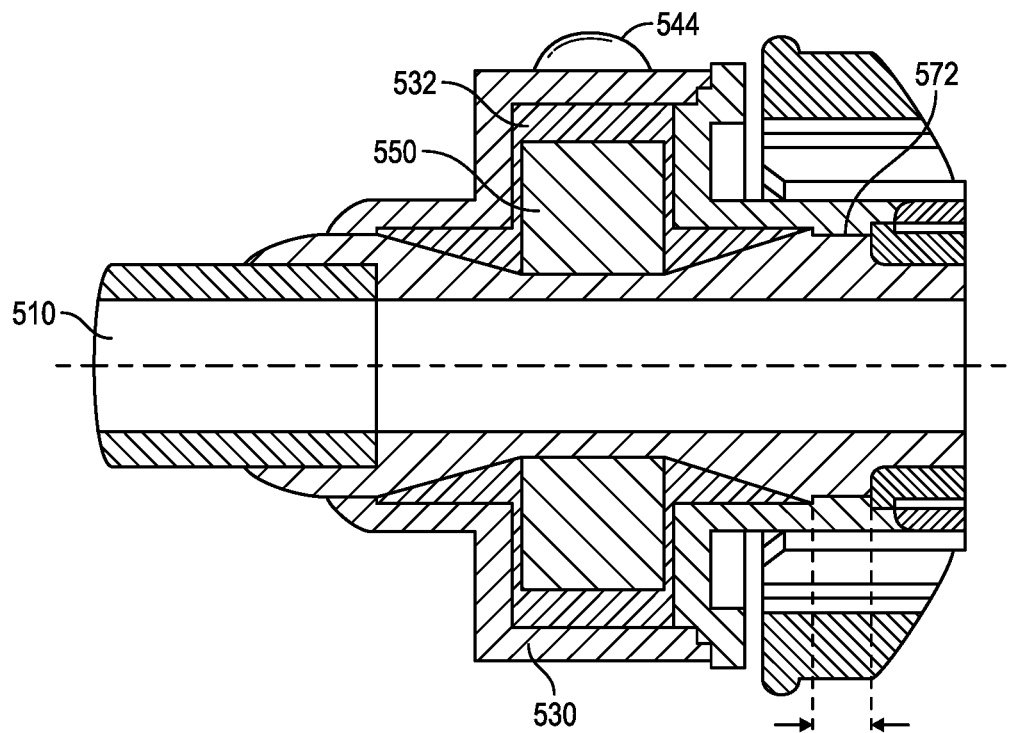
FIG. 28 shows a side view cross section of a distal end of an exemplary catheter assembly disclosed herein with a wetting device.

FIG. 28 represents a side view cross-section of a wetting device and catheter assembly at the distal end of the catheter tube, which would be the end for insertion into a urethra. This side view cross section may be a view of the internal contents of catheter assembly 500 as shown in FIG. 27. Cather tube 510 may pass through wetting applicator 550 which is contained in chamber 532, enclosed by enclosure 530. Feature 544 is an optional filling port for adding a wetting agent to the wetting applicator 550. Feature 572 is the proximal part of a tapered connecting tube positioned through the wetting chamber 532.

Figure 29:
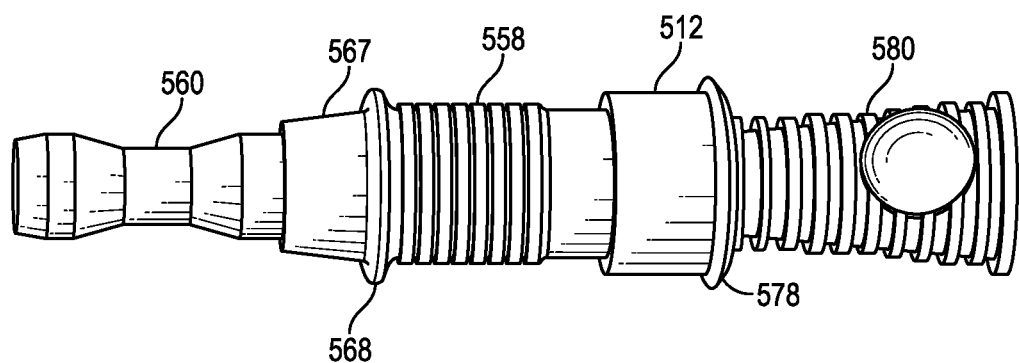
FIG. 29 shows a top view of an exemplary catheter assembly having a wetting device for use with a female urethra. This is a view before extension of the catheter tube and wetting of the catheter tube.

FIG. 29 shows a top view of a catheter assembly, before connector 560 has been pulled through part 558 upon removal of the catheter assembly from its case. The funnel 580 connection (not shown) to connector 560 sits inside locator tip 567, which is part of a locator comprising locator tip 567, locator tip base 568, and locator grip 558. Connector 560 sits inside and seals against the wetting device (not shown) during storage. Connector 560 is pulled through and activates the wetting device, which is attached to the case, to release wetting agent upon removal of the catheter assembly from the case.

Figure 30:
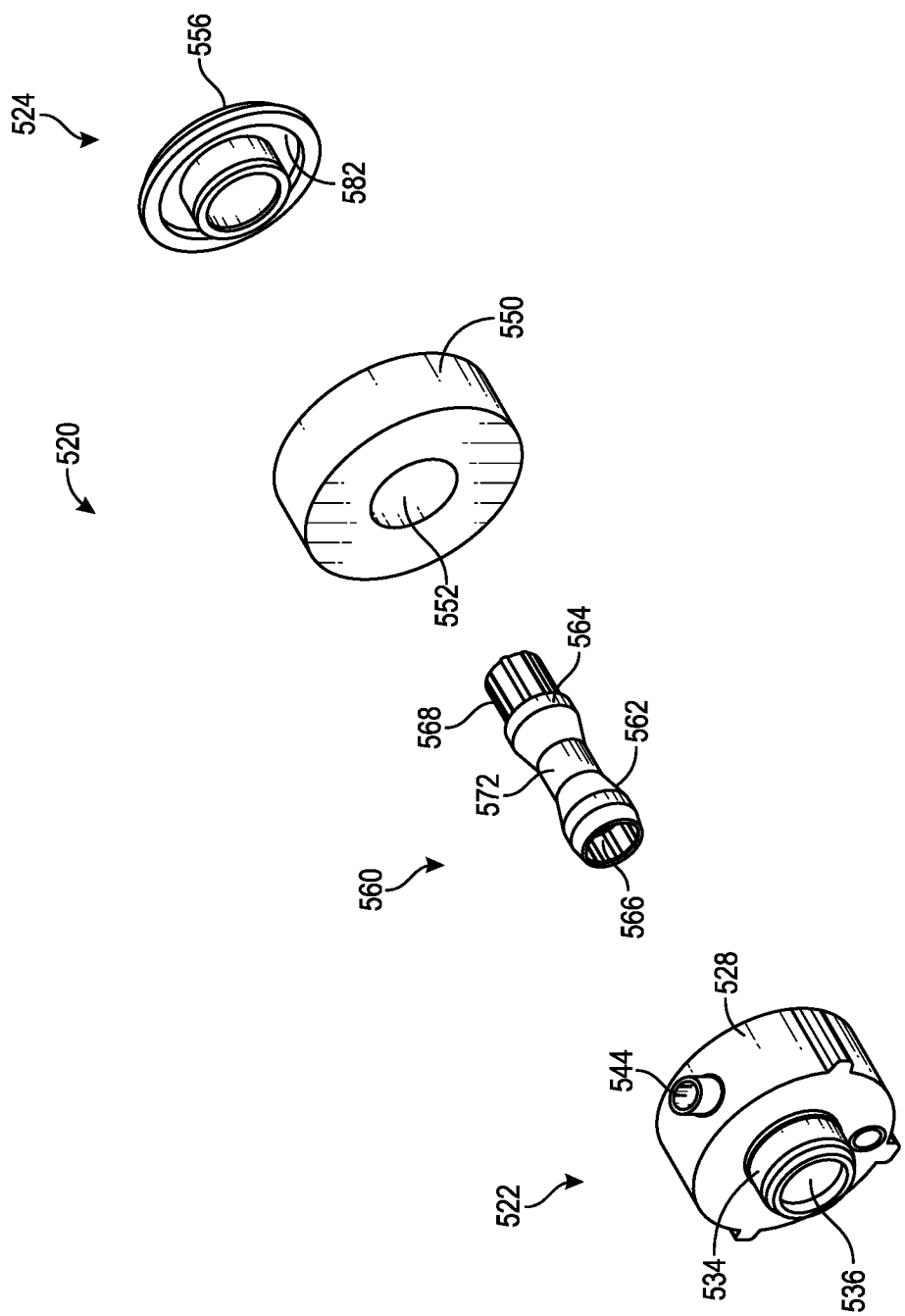
FIG. 30 shows an exploded perspective view of an exemplary wetting device.

FIG. 30 shows an exploded view of wetting device 520. Wetting device 520 may be particularly well suited for a female catheter assembly that is long and cylindrical such as the catheter assembly depicted in FIG. 10, but may also be used for a male catheter assembly. Wetting device 520 has a forward section 522 comprising aperture 536, elongated portion 534 and surface 528 with port 544. Connector 560 has a first end 566, second end 568, plug members 562 and 564, and middle section 572. Middle section 572 may have a smaller circumference than then plug members 562 and 564, such that when assembled and before use, middle section 572 rests within opening 552 without applying any pressure to wetting applicator 550. When the catheter tube is deployed and pulled through opening 552, at least one of the plug members 562 and 564, pass through opening 552, applying pressure to wetting applicator 550, thereby squeezing wetting agent out of the wetting applicator and on to the following catheter tube. Wetting device 520 may comprise rearward section 524 that connects with the forward section 522 to contain the wetting applicator 550. Feature 582 is the inside of the back cover of the wetting device 520; 556 is the back cover of the wetting chamber 532.

Figure 31:
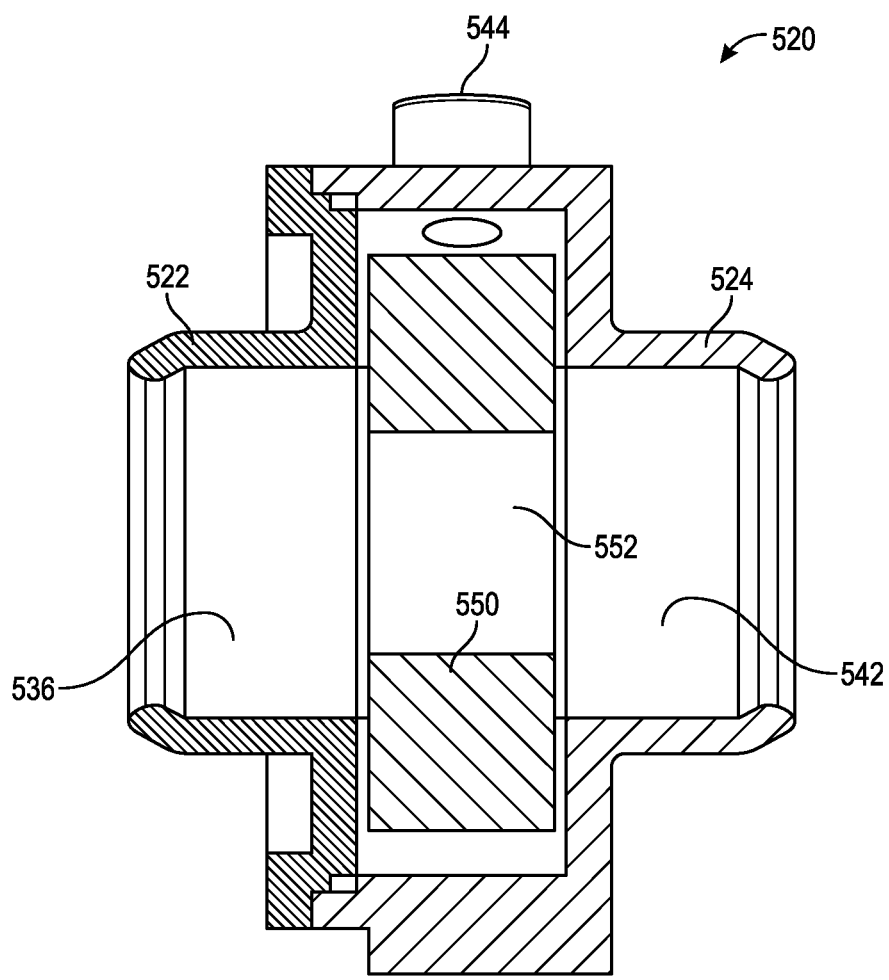
FIG. 31 shows a side view cross section of an exemplary wetting device.

FIG. 31 shows a side view cross section of wetting device 520. Wetting device 520 comprises apertures 536 and 542, wetting applicator 550, wetting applicator opening 552, forward section 522, and rearward section 524, as well as port 544 to introduce wetting agent to wetting applicator 550.

Figure 32:
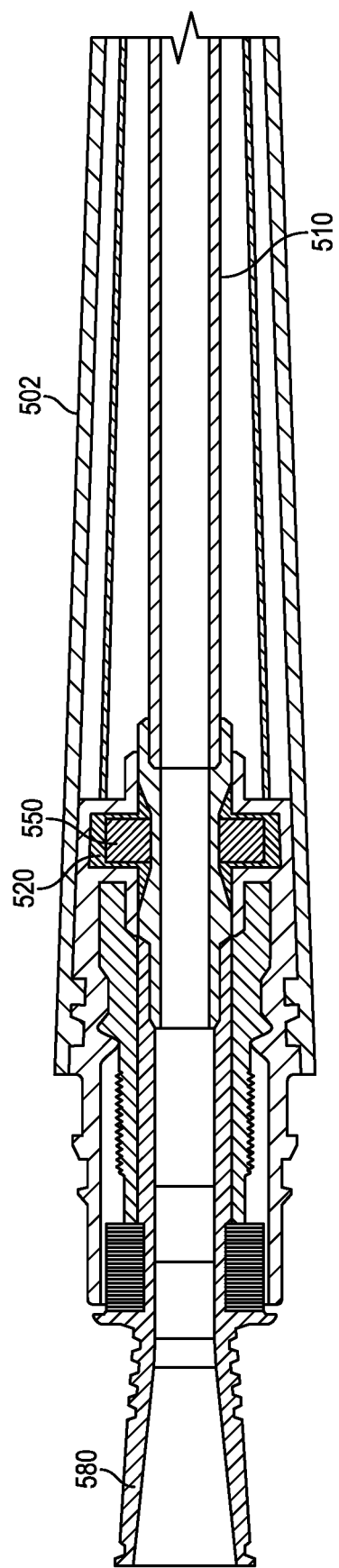
FIG. 32 shows a side view cross section of a catheter assembly comprising a wetting device.

FIG. 32 shows a side view cross section of a catheter assembly including wetting device 520 with wetting applicator 550, funnel 580, a handling feature (outer housing or sleeve) 502, and a catheter tube 510. The circled region shows the joining between the handling feature 502 and the neck. This joining may be hermetic to ensure a sterile seal. The joining may be formed by laser welding. The joining may be formed by ultrasonic welding or any other continuous welding technique.

Figure 33:
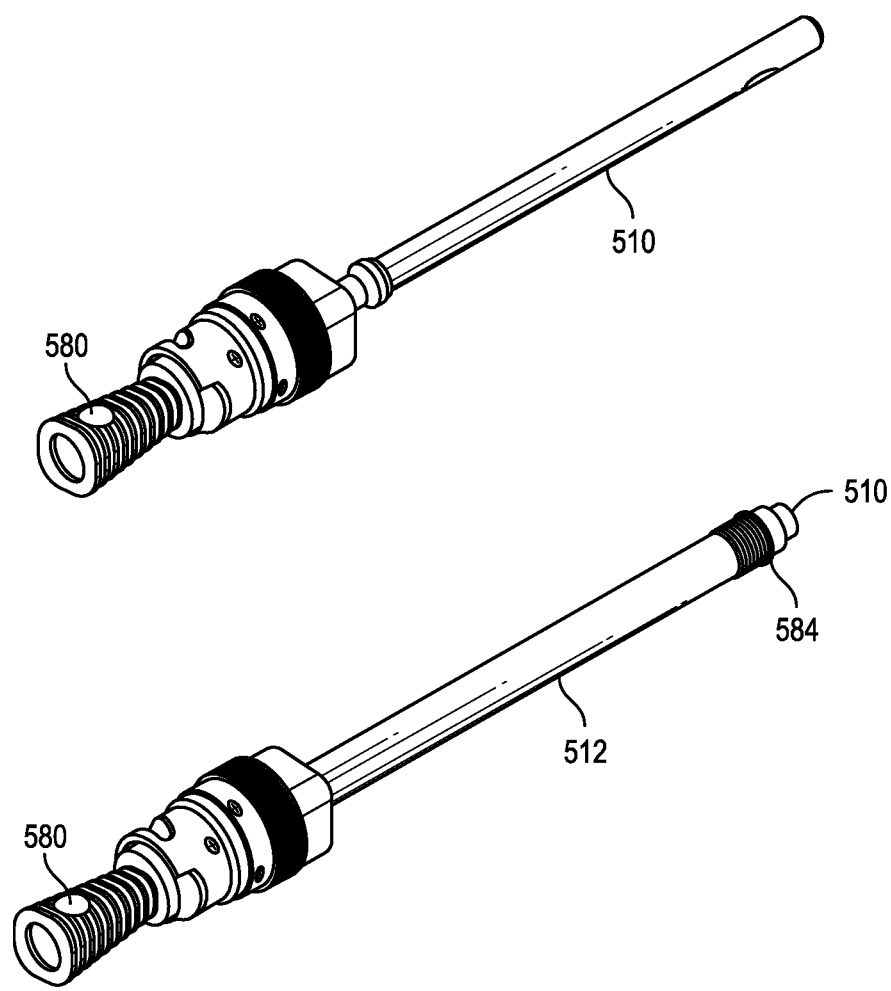
FIG. 33 shows a female catheter assembly with wetting device both in a stored state (before use) and a catheter in use (wetting chamber activated).

FIG. 33 shows an exemplary female catheter assembly in a stored state (top) and an activated state (bottom). The catheter assembly comprises a wetting device disclosed herein between funnel 580 and catheter tube 510. In the stored state, the catheter tube is not covered by sleeve 512. In an activated state, sleeve 512 is pulled over catheter tube 510, via locator tip 584. As the catheter is pulled out of the container, the wetting device is actuated, wetting the catheter tube as the tube passes through the wetting device and out of the container. The sleeve assembly, including the gripper and locator tip, is pulled over the catheter simultaneously or substantially simultaneously as the catheter is lubricated or wetted with the wetting device solution. After use, the catheter tube is inserted back into the container, pushing the sleeve assembly back down to its stored state position.

It should be noted that the terms "first", "second", "third", "forward", "rearward", "upper", "lower", "top" and "bottom" and the like have been used herein to modify various elements. However, these modifiers do not imply a spatial, sequential, or hierarchical order to the modified elements unless specifically stated.

While the present disclosure has been described with reference to one or more exemplary embodiments, it will be understood by those skilled in the art that various changes can be made and equivalents can be substituted for elements thereof without departing from the scope of the present disclosure. In addition, many modifications can be made to adapt a particular situation or material to the teachings of the disclosure without departing from the scope thereof. Therefore, it is intended that the present disclosure is not limited to the particular embodiment(s) disclosed as the best mode contemplated, but that the present disclosure will include all embodiments falling within the scope of the appended claims.

What is claimed is:

1. A wetting device for wetting a catheter, comprising:
   an enclosure bounding the wetting device and enclosing a chamber, the enclosure having at least two wetting device apertures in a surface of the enclosure through which a catheter tube passes;
   a wetting applicator disposed in the chamber, wherein the wetting applicator is infused with wetting agent and is configured to release wetting agent when compressed;
   a port disposed through the enclosure thereof for loading wetting agent into the chamber; and
   a connector that extends through an opening in the wetting applicator, wherein the connector applies pressure to the wetting applicator to release wetting agent as the tube is moved through the wetting device.

2. The wetting device according to claim 1, wherein the port comprises a one-way valve to only permit flow into the chamber.

3. The wetting device according to claim 1, wherein the enclosure is sufficiently rigid to prevent external pressure on the contents of the enclosure.

4. The wetting device according to claim 1, wherein the enclosure is leak-proof.

5. The wetting device according to claim 1 wherein the at least two wetting device apertures are configured to be sufficiently snug around the catheter tube, such that any wetting agent within the enclosure of the wetting device cannot pass though the wetting device apertures unless it is on the catheter tube.

6. The wetting device according to claim 1, further comprising a plug.

7. The wetting device according to claim 6 wherein the plug creates an interference fit with a seal of the chamber.

8. The wetting device according to claim 1 wherein the wetting device wets the catheter tube during removal of the catheter from a package.

9. The wetting device according to claim 8 wherein the package is a case.

10. The wetting device according to claim 1, wherein a portion of the wetting device enclosure defines the perimeter of the wetting device aperture.

11. The wetting device according to claim 10 wherein the portion of the wetting device enclosure comprises a different material from that of the remaining enclosure.

12. The wetting device according to claim 1, wherein at least one of the two apertures is conical so that the inner diameter of the one aperture decreases in a direction away from the chamber.

13. The wetting device according to claim 1, wherein the wetting agent is a liquid.

14. The wetting device according to claim 1, wherein the catheter is a female urinary catheter.

15. A system comprising a wetting device and a tube, the system comprising:
   an enclosure enclosing a chamber having at least two apertures through which the tube can traverse;
   a wetting applicator located in the chamber having an opening through which the tube can traverse;
   a port disposed through the enclosure thereof for loading wetting agent into the chamber; and
   a connector connecting the tube to a funnel;
   wherein the wetting applicator is configured to release a wetting agent upon pressure applied within the chamber to the wetting applicator;
   wherein the connector is positioned within the wetting device and has a first plug at a first end and a second plug at a second end; and
   wherein the first plug and the second plug seal the wetting device until the connector is pulled through the wetting device.

16. The system of claim 15, further comprising a handling sleeve, wherein the handling sleeve extends over the tube as the tube is removed from the enclosure.

17. The system of claim 15, wherein the port comprises a one-way valve to only permit flow into the chamber.

18. A system comprising a wetting device and a tube, the system comprising:
- an enclosure enclosing a chamber having at least two apertures through which the tube can traverse;
- a wetting applicator located in the chamber having an opening through which the tube can traverse;
- a port disposed through the enclosure thereof for loading wetting agent into the chamber; and
- a connector connecting the tube to a funnel;
- wherein the wetting applicator is configured to release a wetting agent upon pressure applied within the chamber to the wetting applicator; and
- wherein the connector applies pressure to the wetting applicator to release the wetting agent as the tube is moved through the wetting device.

* * * * *